United States Patent [19]

Kunz et al.

[11] Patent Number: 5,260,423

[45] Date of Patent: Nov. 9, 1993

[54] SUBSTITUTED BENZO-1,2,3-THIADIAZOLES

[75] Inventors: Walter Kunz, Oberwil; Rolf Schurter, Binningen, both of Switzerland

[73] Assignee: Ciba-Geigy Corporation, Ardsley, N.Y.

[21] Appl. No.: 951,300

[22] Filed: Sep. 24, 1992

Related U.S. Application Data

[63] Continuation of Ser. No. 841,676, Feb. 26, 1992, abandoned.

[30] Foreign Application Priority Data

Mar. 6, 1991 [CH] Switzerland .......................... 666/91

[51] Int. Cl.⁵ .......................................... C07D 285/14
[52] U.S. Cl. .................................. 534/618; 548/110; 548/126
[58] Field of Search .................. 548/110, 126; 534/618

[56] References Cited

U.S. PATENT DOCUMENTS

| | | | |
|---|---|---|---|
| 4,931,581 | 6/1990 | Schurter et al. | 548/126 |
| 5,051,436 | 9/1991 | Kunz et al. | 548/126 X |
| 5,066,661 | 11/1991 | Kunz et al. | 548/126 X |

FOREIGN PATENT DOCUMENTS

| | | | |
|---|---|---|---|
| 1695786 | 4/1971 | Fed. Rep. of Germany | |
| 1176799 | 1/1970 | United Kingdom | |

OTHER PUBLICATIONS

Clarke et al., Chemical Abstracts (1980) 220643x.
J. Chem. Research(s), p. 197 (1980).
J. Chem. Soc. 1970 pp. 2250-2253.
J. Chem. Soc. 1971 pp. 3997-3999.
J. Chem. Res. 1980 pp. 190-191.
J. Chem. Res. 1980 pp. 2845-2866.

*Primary Examiner*—Richard L. Raymond
*Attorney, Agent, or Firm*—Edward McC. Roberts; Marla J. Mathias

[57] ABSTRACT

Compositions comprising, as active ingredients, compounds of the formula I

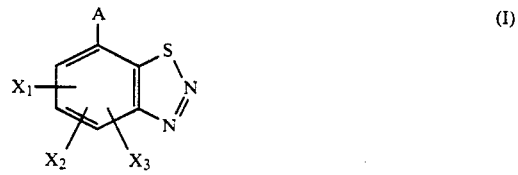

in which:

$X_1$, $X_2$ and $X_3$ independently of one another are hydrogen, methyl, methoxy, methylthio, halogen or nitro;

A is $C_1-C_2$alkyl which is substituted by a maximum of 3 X—$C_1-C_4$alkyl groups, methyl which is substituted by 2 or 3 halogen atoms, ethyl which is substituted by hydroxyl and/or not more than 4 halogen atoms; vinyl which is unsubstituted or substituted by not more than 3 halogen atoms; furthermore ethynyl, propargyl, formyl, acetyl, acetyl which is substituted by not more than 3 halogen atoms, or one of the groups $C(R)=N-N(R_2)R_3$, $C(N=N-U_1)=N-N-H-U_1$, $CH(R)-[N(R_1)]_n-N(R_2)R_3$, $C(R)(CN)OR_4$, $C(R)=N(O)_nR_3$, $CH(R)-O-N=C(R_1)R_2$, $CH(R)-O-N=C(CN)-CONH-R_5$, $C(R_6)=N-(O)_nR$, $CH(R)-Y-E-R_3$, $CO-[C(OR)_2]_nQ$, $C(Q)=CH-OR$ or $T-Q$;

in which furthermore:

n is zero or 1;

X and Y independently of one another are oxygen or sulfur;

R and $R_1$ independently of one another are hydrogen or $C_1-C_2$alkyl;

$R_2$ is hydrogen, $C_1-C_8$alkyl, $C_3-C_6$alkenyl, $C_3-C_6$alkynyl, $C_3-C_7$cycloalkyl, benzyl or cyano;

$R_3$ is hydrogen, $C_1-C_6$alkyl, $C_3-C_6$alkenyl, $C_3-C_6$alkynyl, $C_3-C_7$cycloalkyl, benzyl or is an aryl radical U;

$R_4$ is hydrogen, $C_1-C_6$alkyl, $Si(C_1-C_6alkyl)_3$ or $OCOC_1-C_3$alkyl;

$R_5$ is hydrogen or $CONHR_1$;

$R_6$ is $N(R_1)R_2$, hydrazino or Q;

E is CO or $SO_2$;

U and $U_1$ independently of one another are a phenyl (List continued on next page.)

ABSTRACT radical which is unsubstituted or monosubstituted or polysubstituted by identical or different substituents from the series comprising methyl, methoxy, halogen, trifluoromethyl, nitro or cyano;

T is $C_1$–$C_2$alkylene, methylene which is substituted by amino, hydroxyl or halogen, the substituents being independent of one another, or is ethenylene which is unsubstituted or substituted by halogen or cyano;

Q is COXR or cyano.

The novel compositions have crop-protecting properties and are particularly suitable for protecting plants against infestation by phytopathogenic microorganisms such as fungi, bacteria and viruses.

5 Claims, No Drawings

SUBSTITUTED BENZO-1,2,3-THIADIAZOLES

This application is a continuation of application Ser. No. 841,676, filed Feb. 26, 1992, now abandoned.

The present invention relates to novel substituted benzo-1,2,3-thiadiazole derivatives of the formula I below. The invention furthermore relates to the preparation of these substances and to the compositions comprising, as active ingredients, at least one of these compounds. Moreover, the invention relates to the preparation of the abovementioned compositions and to the use of the active ingredients or of the compositions for protecting plants against infestations by harmful microorganisms, in particular plant-injurious fungi.

The compositions according to the invention comprise, as active ingredients, compounds of the general formula I

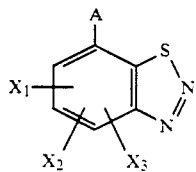 (I)

in which:

$X_1$, $X_2$ and $X_3$ independently of one another are hydrogen, methyl, methoxy, methylthio, halogen or nitro;

A is $C_1$-$C_2$alkyl which is substituted by a maximum of 3 X-$C_1$-$C_4$alkyl groups, methyl which is substituted by 2 or 3 halogen atoms, ethyl which is substituted by hydroxyl and/or not more than 4 halogen atoms, vinyl which is unsubstituted or substituted by not more than 3 halogen atoms; furthermore ethynyl, propargyl, formyl, acetyl, furthermore acetyl which is substituted by not more than 3 halogen atoms, or one of the groups $C(R)=N-N(R_2)R_3$, $C(N=N-U_1)=N-NH-U_1$, $CH(R)-[N(R_1)]_n-N(R_2)R_3$, $C(R)(CN)OR_4$, $C(R)=N(O)_nR_3$, $CH(R)-O-N=C(R_1)R_2$, $CH(R)-O-N=C(C-N)-CONH-R_5$, $C(R_6)=N-(O)_nR$, $CH(R)-Y-E-R_3$, $CO-[C(OR)_2]_nQ$, $C(Q)=CH-OR$ or $T-Q$; in which furthermore:

n is zero or 1;

X and Y independently of one another are oxygen or sulfur;

R and $R_1$ independently of one another are hydrogen or $C_1$-$C_2$alkyl;

$R_2$ is hydrogen, $C_1$-$C_8$alkyl, $C_3$-$C_6$alkenyl, $C_3$-$C_6$alkynyl, $C_3$-$C_7$cycloalkyl, benzyl or cyano;

$R_3$ is hydrogen, $C_1$-$C_6$alkyl, $C_3$-$C_6$alkenyl, $C_3$-$C_6$alkynyl, $C_3$-$C_7$cycloalkyl, benzyl or is an aryl radical U;

$R_4$ is hydrogen, $C_1$-$C_6$alkyl, $Si(C_1$-$C_6$alkyl$)_3$ or $OCOC_1$-$C_3$alkyl;

$R_5$ is hydrogen or $CONHR_1$;

$R_6$ is hydrazino, $N(R_1)R_2$ or Q;

E is CO or $SO_2$;

U and $U_1$ independently of one another are a phenyl radical which is unsubstituted or monosubstituted or polysubstituted by identical or different substituents from the series comprising methyl, methoxy, halogen, trifluoromethyl, nitro or cyano;

T is $C_1$-$C_2$alkylene, methylene which is substituted by amino, hydroxyl or halogen, the substituents being independent of one another, or is ethenylene which is unsubstituted or substituted by halogen or cyano;

Q is COXR or cyano.

Halogen is fluorine, chlorine, bromine or iodine, preferably fluorine, and then in the sequence chlorine, bromine and iodine. Halogen as substituent in individual radicals can be represented up to 3 times.

Alkyl itself or as a component of another substituent is to be understood as meaning straight-chain and branched alkyl radicals. Depending on the number of carbon atoms indicated, these represent for example the following preferred groups: methyl, ethyl as well as the isomers of propyl, butyl, pentyl or hexyl, for example isopropyl, isobutyl, tert-butyl, sec-butyl or isopentyl.

Akenyl is, for example, prop-1-enyl, allyl, but-1-enyl, but-2-enyl or but-3-enyl, and alkynyl is, for example, prop-2-ynyl, but-1-ynyl or pent-4-ynyl.

Cycloalkyls which may be mentioned are, for example, cyclopropane, cyclobutane, cyclopentane, cyclohexane or cycloheptane, preferably cyclopropane, cyclopentane and cyclohexane.

Based on their particular crop-protecting properties, the active ingredients of the formula I can be divided into the following, preferred groups:

1. Compounds in which:

$X_1$, $X_2$ and $X_3$ independently of one another are hydrogen or fluorine;

A is $C_1$-$C_2$alkyl which is substituted by a maximum of 3 X-$C_1$-$C_4$alkyl groups, methyl which is substituted by 2 or 3 halogen atoms, ethyl which is substituted by hydroxyl and/or not more than 4 halogen atoms, vinyl which is unsubstituted or substituted by not more than 3 halogen atoms; furthermore ethynyl, propargyl, formyl, acetyl, or one of the groups $C(R)=N-N(R_2)R_3$, $C(N=N-U_1)=N-NH-U$, $CH(R)-[N(R_1)-]_n-N(R_2)R_3$, $C(R)(CN)OR_4$, $C(R)=N(O)_nR_3$, $CH(R)-O-N=C(R_1)R_2$, $CH(R)-O-N=C(C-N)-CONH-R_5$, $C(R)_6=N(O)_nR$, $CH(R)-Y-E-R_3$, $CO-[C(OR)_2]_nCOxR$, $C(Q)=CH-OR$ or $T-Q$; in which furthermore:

n is zero or 1;

X and Y are oxygen;

R and $R_1$ independently of one another are hydrogen or $C_1$-$C_2$alkyl;

$R_2$ is hydrogen, $C_1$-$C_4$alkyl, $C_3$-$C_4$alkenyl, $C_3$-$C_4$alkynyl, $C_3$-$C_6$cycloalkyl or benzyl;

$R_3$ is hydrogen, $C_1$-$C_4$alkyl, $C_3$-$C_4$alkenyl, $C_3$-$C_4$alkynyl, $C_3$-$C_6$cycloalkyl or a phenyl radical which is substituted by identical or different substituents from the series comprising methyl, halogen or trifluoromethyl;

$R^4$ is hydrogen, $C_1$-$C_3$alkyl or $Si(C_1$-$C_2$alkyl$)_3$;

$R_5$ is hydrogen or $CONHC_1$-$C_3$alkyl;

$R_6$ is $N(R)R_1$, hydrazino or Q;

U and $U_1$ independently of one another are a phenyl radical which is substituted by methyl, halogen, nitro or trifluoromethyl;

E is CO;

T is methylene, methylene which is substituted by amino or ethenylene;

Q is COOR or cyano.

2. Compounds in which:

$X_1$, $X_2$ and $X_3$ are hydrogen;

A is methyl which is substituted by a maximum of 2 X-$C_1$-$C_4$alkyl groups, methyl which is substituted by 2 or 3 fluorine or chlorine atoms, ethyl which is substituted by hydroxyl or 1 to 4 halogen atoms, or formyl, acetyl, or one of the groups $C(R)=N-N(R_2)R_3$, $CH(R)-[N(R_1)]_n-N(R_2)R_3$, $C(R)(CN)OR_4$, $C(R)=N-R_3$, $CH(R)-O-N=C(R_1)R_2$, $CH(R)-O-N=C(CN)-CONHR_5$, $C(R_6)=N(O)_nR$, $CH(R)-Y-E-R_3$, $CO[C(OR)_2]_nCOXR$, $C(COOR)=CH-OR$ or T-Q; in which furthermore:

n is 1;
X is oxygen;
R and $R_1$ independently of one another are hydrogen or methyl;
$R_2$ is hydrogen, $C_1-C_2$alkyl, allyl, propargyl, cyclopropyl or benzyl;
$R_3$ is hydrogen, $C_1-C_2$alkyl, allyl, propargyl, cyclopropyl, or a phenyl radical which is substituted by identical or different substituents from the series comprising methyl, fluorine, chlorine or trifluoromethyl;
$R_4$ is hydrogen, $C_1-C_2$alkyl or $Si(CH_3)_3$;
$R_5$ is hydrogen or $CONH-C_1-C_2$alkyl;
$R_6$ is amino or Q;
Y is oxygen;
E is CO;
T is methylene or cyano;
Q is $COOCH_3$ or CN.

3. Compounds in which:
$X_1$, $X_2$ and $X_3$ are hydrogen;
A is methyl which is substituted by a maximum of 2 $X-C_1-C_2$alkyl groups, methyl which is substituted by 2 or 3 fluorine atoms, ethyl which is substituted by hydroxyl or chlorine, or formyl, or one of the groups $C(R)=N-N(R_2)R_3$, $CH(R)-[N(R_1)]_n-N(R_2)R_3$, $C(R)(CN)OR_4$, $C(R)=N(O)_nR_3$, $CH(R)-O-N=C(R_1)R_2$, $C(R_6)=N-OR$, $CH(R)-Z-E-R_3$, $CO[C(OR)_2]_nCOXR$ or T-Q; in which furthermore:

n is 1;
X is oxygen;
R and $R_1$ independently of one another are hydrogen or methyl;
$R_2$ is hydrogen, methyl, allyl, cyclopropyl or benzyl;
$R_3$ is hydrogen, methyl, allyl, cyclopropyl, or a phenyl radical which is substituted by identical or different substituents from the series comprising methyl, fluorine, chlorine or trifluoromethyl;
$R_4$ is hydrogen, methyl or $Si(CH_3)_3$;
$R_5$ is hydrogen or $CONH-CH_2-CH_3$;
$R_6$ is amino;
Y is oxygen;
E is CO;
T is methylene;
Q is cyano or $COOCH_3$.

The following active ingredients of the formula I are distinguished by particularly advantageous crop-protecting properties:
7-formyl-1,2,3-benzothiadiazole; (known)
7-acetoxymethyl-1,2,3-benzothiadiazole;
7-[(2-cyanoacetamidyl)iminooxymethyl]-1,2,3-benzothiadiazole;
7-(N-methoxyiminomethyl)-1,2,3-benzothiadiazole;
7-(N-methoxyiminohydroxymethyl)-1,2,3-benzothiadiazole;
7-methoxymethyl-1,2,3-benzothiadiazole;
3-(7-benzo-1,2,3-thiadiazolyl)acrylic acid;
7-cyanomethyl-1,2,3-benzothiadiazole;
7-trichloromethyl-1,2,3-benzothiadiazole;
7-dichloromethyl-1,2,3-benzothiadiazole;
benzo-1,2,3-thiadiazole-7-(N-hydroxycarboximideamide);
benzo-1,2,3-thiadiazole-7-(N-methoxyhydroxamic acid);
2-(benzo-1,2,3-thiadiazolyl)-2-hydroxyiminoacetonitrile;
5-fluoro-benzo-1,2,3-thiadiazole-7-carbaldehyde;
6-fluoro-benzo-1,2,3-thiadiazole-7-carbaldehyde;
4-fluoro-benzo-1,2,3-thiadiazole-7-carbaldehyde;
N,N-diphenyl-C-[benzo-1,2,3-thiadiazol-7'yl]formazane;
7-acetylbenzo-1,2,3-thiadiazole;
7-(bromoacetyl)benzo-1,2,3-thiadiazole.

Compounds which come under the formula I are novel with the exception of:
7-formyl-1,2,3-benzothiadiazole;
7-acetyl-1,2,3-benzothiadiazole;
6-chloro-7-formyl-1,2,3-benzothiadiazole;
6-methylthio-7-formyl-1,2,3-benzothiadiazole;
4-bromo-6-chloro-7-formyl-1,2,3-benzothiadiazole;
6-methoxy-7-formyl-1,2,3-benzothiadiazole;
7-hydroxyiminomethyl-1,2,3-benzothiadiazole;
6-methoxy-7-hydroxyiminomethyl-1,2,3-benzothiadiazole,
7-dibromoacetyl-1,2,3-benzothiadiazole.

The novel compounds form a special part of the present invention.

The compounds which were designated above as not novel are known from the following literature: J. Chem. Res. 1980, 191 and 2845; J. Chem. Soc. 1971, 3994; British Patent Application 1 176 799; Dutch Patent Specification 67 16077, and German Offenlegungsschrift 1 695 786.

The compounds of the formula I are prepared as follows:

1.1 Nitration of a compound of the formula II

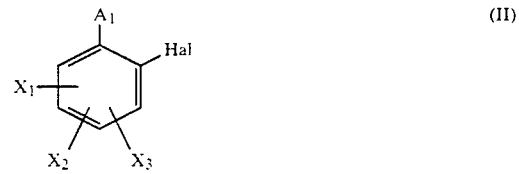

with $HNO_3$ with or without an addition of $H_2SO_4$ and/or solvents such as $CH_2Cl_2$, at temperatures from $-20°$ to $80°$ C., to give a compound of the formula III

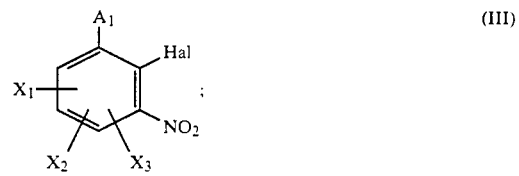

1.2 Reaction of a compound of the formula III with a compound of the formula IIIa MSL  (IIIa)

in inert solvents with or without a base at temperatures of $-5°$ to $50°$ C. to give a compound of the formula IV

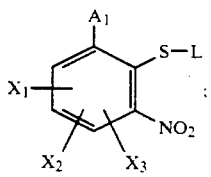
(IV)

1.3 Reduction of a compound of the formula IV with hydrogen in the presence of a catalyst or with iron powder in acetic acid in inert solvents at temperatures from 0° to 120° C. to give a compound of the formula V

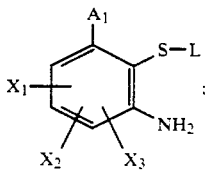
(V)

1.4 Diazotisation of a compound of the formula V with $NaNO_2$ in the presence of an acid in water and additionally with inert solvents or without the latter, at temperatures of −30° to 50° C., to give a compound of the formula Ia

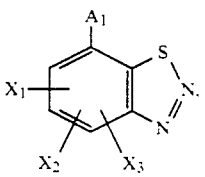
(Ia)

where in the above formulae $A_1$ means the radicals A mentioned under formula I with the exception of those which comprise free hydroxyl, thiol or NH groups, and those groups which are unstable in aqueous-acidic medium, for example the acetals or ketals, and $X_1$, $X_2$ and $X_3$ have the meanings given under formula I;

2.1 Compounds of the formulae Ib, Ic and Id

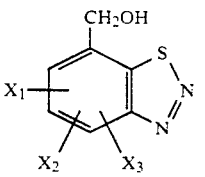
(Ib)

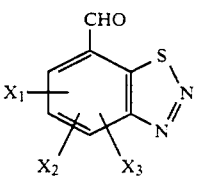
(Ic)

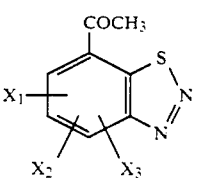
(Id)

are prepared:

2.1.1. by reacting a compound of the formula VI

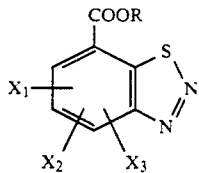
(VI)

a) with a reducing agent in inert solvents at −20° to 120° C., preferably 0° to 80° C., for example.

b) with sodium borohydride in inert solvents, for example tetrahydrofuran or dioxane, in the presence of water at −20° C. to 100° C., preferably 0° to 80° C., to give a compound of the formula Ib; or by reacting the acid chloride of the formula VII′

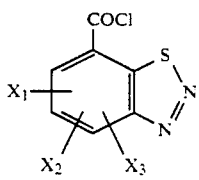
(VII′)

with hydrogen in a Rosenmund reaction in an inert solvent, for example tetrahydrofuran, in the presence of a base, for example lutidine, by means of a catalyst, for example palladium on barium sulfate, at −20° to 120° C., preferably 0° to 120° C., furthermore preferably 0° to 80° C., to give a compound of the formula Ib, and 2.1.2 by oxidising a compound of the formula Ib with an oxidant, for example manganese dioxide, in an inert solvent, for example chloroform, or cerium ammonium nitrate in a mixture of acetic acid and water at 0° to 110° C., preferably 20° to 100° C., to give a compound of the formula Ic.

2.1.3 by reacting a nitrile of the formula V

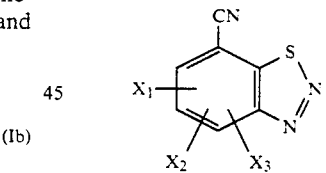
(V)

or a hydroxamic acid derivative of the formula VIII

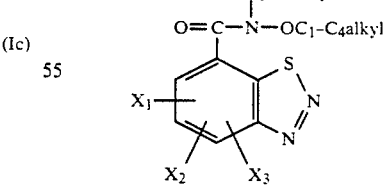
(VIII)

with a Grignard reagent, $CH_3Mg$-halogen, in an inert solvent, for example an open-chain or cyclic ether (for example tetrahydrofuran or dioxane) at −50° to 130° C., preferably −10° or 80° C., to give a compound of the formula Id, where the radicals $X_1$, $X_2$ and $X_3$ which occur in the above-described formulae have the meanings given under formula I and R in formula VI is hydrogen or methyl;

3.1 Compounds of the formula Ie

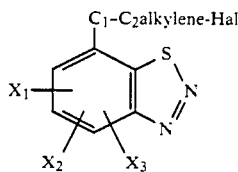

are prepared: by reacting a compound of the formula Ib'

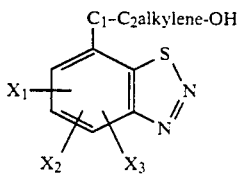

with a halogenating agent, for example thionyl halide, in inert solvents, such as dichloromethane, in the presence of a base, for example pyridine at −20° to 150° C., where Hal is halogen and the radicals $X_1$, $X_2$ and $X_3$ have the meanings given under formula I;

3.2 Compounds of the formula If

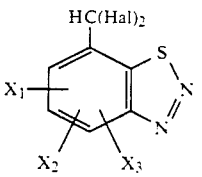

are prepared: by reacting a compound of the formula Ic

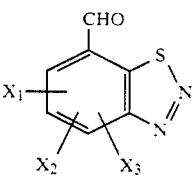

with a halogenating agent, for example thionyl halide, in inert solvents, for example dichloromethane, in the presence of a base, for example pyridine, at −20° to 150° C., where Hal is halogen and the radicals $X_1$, $X_2$ and $X_3$ have the meanings given under formula I;

3.3 Compounds of the formula Ig

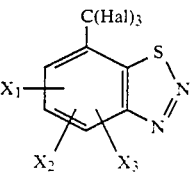

are prepared:

3.3.1 by reacting a compound of the formula VI'

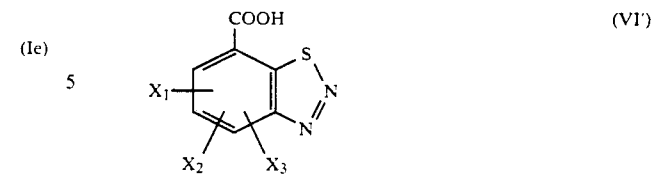

with a halogenating agent, for example phosphorus pentahalide, phenylphosphorus oxydichloride or phenyleneoxyphosphorus dichloride, in inert solvents or without the latter, at 20° to 250° C., preferably 80° to 200° C.; or 3.3.2 by reacting a compound of the formula Ig with sulfur tetrafluoride in the presence of hydrofluoric acid in an autoclave at 0° to 250° C., where Hal is halogen and R is hydrogen or methyl and the radicals $X_1$, $X_2$ and $X_3$ have the meanings given under formula I;

3.4 Compounds of the formula Ih

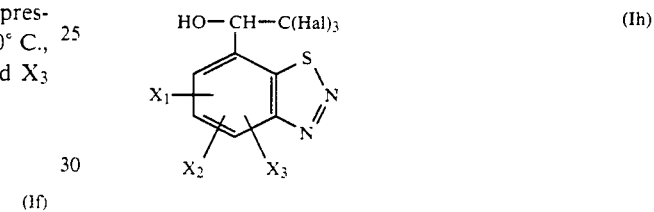

are prepared by reacting a compound of the formula Ic with 2,2,2-trihaloacetic acid in dipolar aprotic solvents, for example hexamethylphosphoric triamide or dimethyl sulfoxide, at 0° to 150° C., preferably 20° to 100° C.; and 3.5 Compounds of the formula Ii

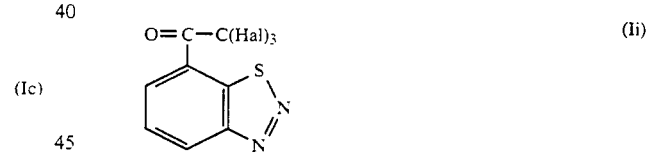

are prepared:

3.5.1 by reacting a compound of the formula Id with a halogenating agent, for example elemental halogen or sulfonyl halide, with or without an addition of free radicals, or 3.5.2 by oxidising a compound of the formula Ih with an oxidant, for example $MnO_2$ or pyridinium chlorochromate, in an inert solvent such as chloroform, at 20° to 150° C.; where in the above formulae Hal is fluorine, chlorine, bromine or iodine;

4. Compounds of the formulae $Ik_1$ and $Ik_2$

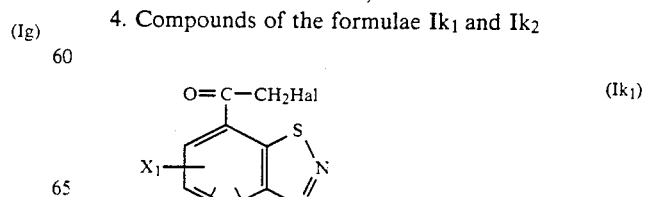

-continued

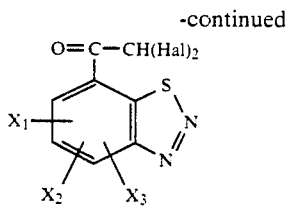 (Ik2)

are prepared by reacting in each case one compound of the formula Id with stoichiometrically matched amounts of a halogenating agent, for example elemental halogen or sulfonyl halide, with or without an addition of free radicals, where Hal is halogen and $X_1$, $X_2$ and $X_3$ have the meanings given under formula I; and 5.1 Compounds of the formula $II_1$

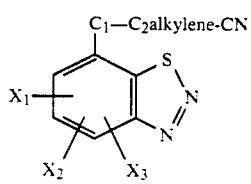 (II₁)

are prepared by reacting compounds of the formula Ie with cyanide compounds of the formula MCN in inert solvents at $-10°$ to $120°$ C., it also being possible for the reaction to be carried out in a 2-phase system, for example in $CHCl_3/H_2O$, in the presence of a quaternary ammonium salt, for example tetrabutylammonium chloride or tetrabutylammonium iodide; and 5.2 Compounds of the formulae $II_2$ and $II_3$

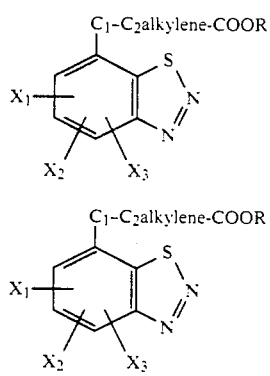

are prepared by hydrolysing nitriles of the formula $II_1$ to give the compounds of the formula $II_2$, and esterification thereof with compounds of the formula ROH, where in the above formulae M is an alkali metal cation or ammonium cation, R is $C_1$-$C_4$alkyl and $X_1$, $X_2$ and $X_3$ have the meanings given under formula I;

6.1 Compounds of the formulae $Im_1$ and $Im_2$

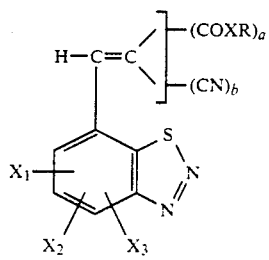 (Im₁)

-continued

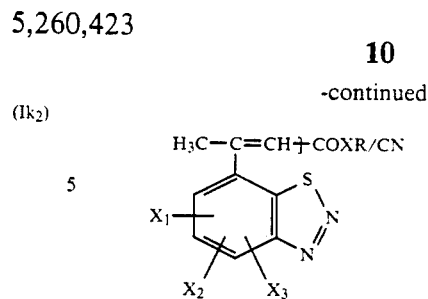 (Im₂)

are prepared by condensing compounds of the formula Ic or Id

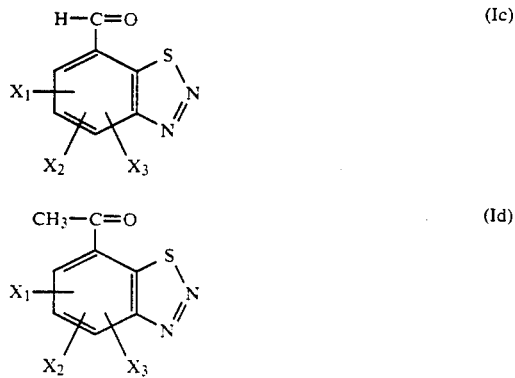

with compounds of the formula

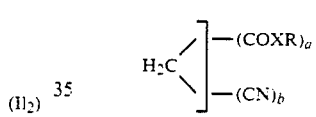

in the presence of catalysts, for example ammonium acetate or lower organic carboxylic acids, as well as bases, for example pyridine or piperidine, with or without an addition of solvents, for example toluene, with or without separation of the water formed, for example by azeotropic distillation or by using a molecular sieve, where $(a+b)=2$ and $a=(2-b)$ and R, X, $X_1$, $X_2$ and $X_3$ have the meanings given under formula I.

If desired, decarboxylation (Knoevenagel reaction) can be effected when a suitable malonic acid derivative or cyano acetic acid derivative is used as the active methylene component. This decarboxylation can be effected in one reaction step or in another reaction step by heating to $30°$ to $300°$ C. with or without inert solvents, following hydrolysis of a COXR— or CN— group to give the COOH— group; and 7.1 Compounds of the formula $In_1$

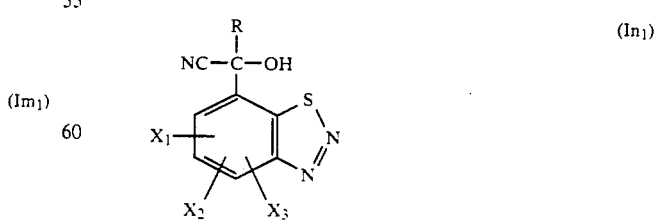 (In₁)

are prepared by reacting compounds of the formulae Ic and Id with alkali metal cyanide or hydrogen cyanide in an inert solvent, for example tetrahydrofuran or methanol, with or without an addition of sodium hydrogen sulfite at −20° to 140° C., preferably 0° to 90° C., or by hydrolysis of silyl esters of the formula In₂

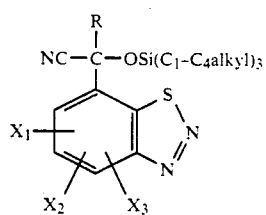

(In₂)

with dilute mineral acids, for example HCl, in inert solvent at −20° to 120° C.;

7.2 Compounds of the formula In₂ are prepared by reacting aldehydes of the formula Ic or ketones of the formula Id with trialkylsilyl cyanide in inert solvents, for example tetrahydrofuran, dioxane, chloroform or dichloromethane, preferably with an addition of catalytic amounts of a metal salt, for example ZnI₂, at −30° to 130° C., preferably −10° C. to 100° C.;

7.3 Compounds of the formula In₃

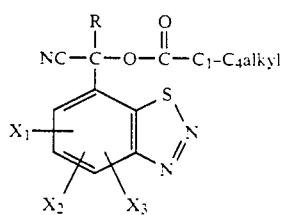

(In₃)

are prepared by reacting compounds of the formula In₁ with acid chlorides or acid anhydrides in the presence of a base, for example triethylamine, and a catalyst, for example 4-dimethylaminopyridine; and 7.4 Compounds of the formula In₄

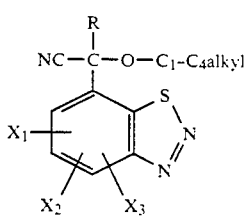

(In₄)

are prepared:

7.4.1 by reacting compounds of the formula In₁ with an alkylating agent, for example a $C_1$-$C_4$alkyl halide, preferably a $C_1$-$C_4$alkyl iodide, in the presence of a base, for example triethylamine or alkali metal carbonate or alkaline earth metal carbonate, in inert solvents at −20° to 100° C.; or 7.4.2 by reacting acetals of the formula In₅

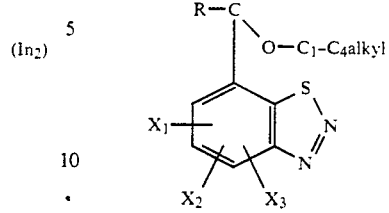

(In₅)

with tri($C_1$-$C_4$alkyl)silyl cyanides in the presence of a Lewis acid, for example boron trifluoride etherate, in inert solvents at −20° to 150° C.;

8.1 Compounds of the formula Io₁

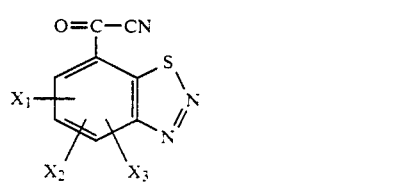

(Io₁)

are prepared by reacting compounds of the formula IX

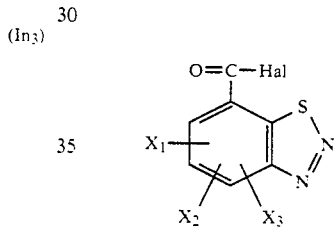

(IX)

with metal salts of the formula $M^{m\oplus}(CN)_m$, in which M is a metal cation, for example $Na^\oplus$, $K^\oplus$, $Ag^\oplus$ or $Pb^{2\oplus}$, in inert solvents at −20° to 120° C., where m is 1 or 2 and Hal is halogen;

8.2 Compounds of the formula Io₂

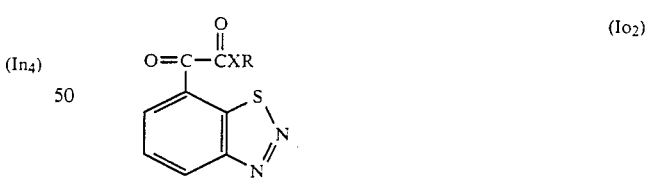

(Io₂)

are prepared:

8.2.1 by oxidising corresponding α-hydroxy compounds, using an oxidant, for example manganese dioxide or pyridinium chlorochromate; or 8.2.2 by acid hydrolysis of compounds of the formula Ii or of compounds of the formula Io₁ with dilute bases, for example solutions of alkali metal hydroxides, alkali metal carbonates, alkaline earth metal hydroxides or alkaline earth metal carbonates, with or without an addition of inert solvents at −10° to 150° C., preferably 20° to 100° C.; or 8.2.3 by reacting compounds of the formula Iq

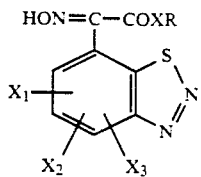
(Iq)

with excess aqueous formaldehyde or with acetone in the presence of an acid, for example HCl, and with or without an addition of an oxidant, for example dichlorodicyanobenzoquinone, selenium dioxide or pyridinium chlorochromate;

8.2.4 by reacting compounds of the formula $Ix_2$

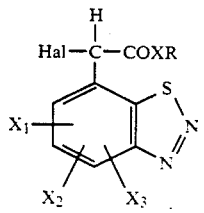
(Ix2)

with alkali metal azide in inert solvents, for example dimethylformamide, at $-20°$ to $50°$ C., to give compounds of the formula

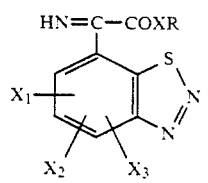

followed by aqueous hydrolysis with or without an addition of a catalyst, for example $CuSO_4$; and 8.3 Compounds of the formula $Io_3$

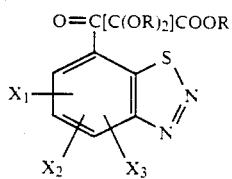
(Io3)

are prepared by reacting compounds of the formula VII

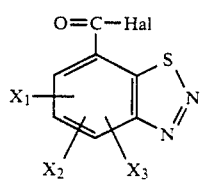
(VII)

with a tetraalkoxyethylene of the formula

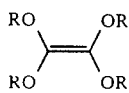

in inert solvents, for example toluene, at $20°$ to $220°$ C.; where Hal is halogen, X is oxygen or sulfur and R is $C_2$-$C_4$alkyl, and $X_1$, $X_2$ and $X_3$ have the meanings given under formula I;

9.1 Compounds of the formula Ip

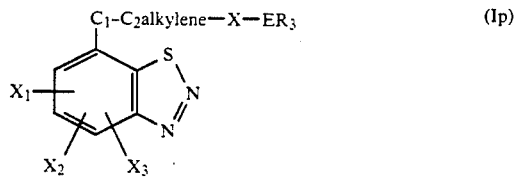
(Ip)

are prepared:

9.1.1 by reacting compounds of the formula Ib with acid chlorides of the formula $R_3$—E—Hal or acid anhydrides of the formula $(R_3$—E$)_2$O in the presence of a base, for example triethylamine, with or without an addition of a catalyst, for example 4-dimethylaminopyridine, in an inert solvent, for example dichloromethane, at $-20°$ to $150°$ C.; or 9.1.2 by reacting compounds of the formula Ie with alkali metal salts of the formula $R_3COXM$ in a dipolar, aprotic solvent, for example N,N-dimethylformamide or dimethylsulfoxide, at $-20°$ to $150°$ C.; where X, E and $R_3$ as well as $X_1$, $X_2$ and $X_3$ have the meanings given under formula I;

10.1 Compounds of the formula $Iq_1$

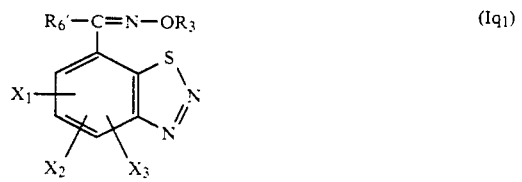
(Iq1)

are prepared by reacting compounds of the formula Ic, Id, Ii, Ik and $Io_2$ with compounds of the formula $NH_2OR_3$ or the hydrochloride thereof in a protic solvent with or without an addition of a base, for example alkali metal carbonate, alkali metal hydroxide or alkali metal oxide, or with or without an addition of an acid such as acetic acid, at $-10°$ to $120°$ C.; where $R_6'$ is hydrogen, methyl, COXR or CN, and X, R and $R_3$ as well as $X_1$, $X_2$ and $X_3$ have the meanings given under formula I; and 10.2 Compounds of the formula $Iq_2$

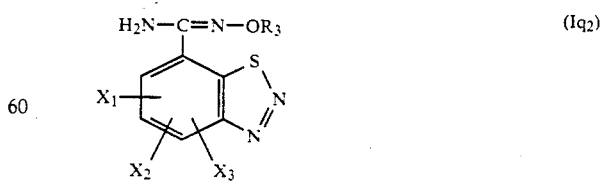
(Iq2)

are prepared by reacting compounds of the formula V with compounds of the formula $H_2N$—$OR_3$ in an inert solvent, for example ethanol, at $-20°$ to $120°$ C.; and 10.3 Compounds of the formula $Iq_3$

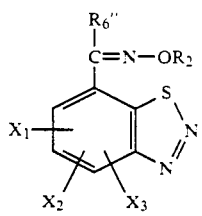
(Iq₃)

are prepared by reacting compounds of the formula II₁, II₂ and II₃ with nitrous acid or with an alkyl ester of nitrous acid, for example iso-amyl nitrite, in the presence of a base, for example an alkali metal hydroxide or alkali metal alcoholate, at $-30°$ to $100°$ C.; it being possible for compounds of the formula Iq₃ in which R₂ is hydrogen to be etherified later in the presence of a base, for example sodium hydride, potassium tert-butylate, alkali metal hydroxide or alkali metal carbonate, in an inert solvent at $-20°$ to $100°$ C., using compounds of the formula R₂—Hal, and where R₆" is CH₃, COXR or CN, R is C₁-C₄alkyl and R₂, X₁, X₂ and X₃ have the meanings given under formula I; and 10.4 Compounds of the formula Iq₄

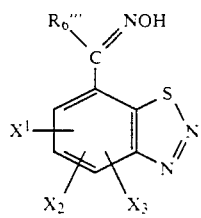
(Iq₄)

in which R₆'" is hydrazino or NR(R₁) are prepared from the benzohydroxamic chlorides Iq'

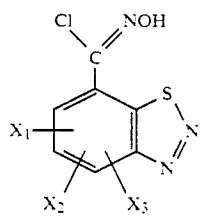
(Iq')

with an amine of the formula NR(R₁) or hydrazine in an inert solvent at $-40°$ to $+100°$ C. Benzohydroxamic chlorides of the formula Iq' are obtained by chlorinating the corresponding aldoximes with a chlorinating agent, for example Cl₂, in a suitable solvent such as dilute hydrochloric acid, at $-60°$ to $+50°$ C.

11.1 Compounds of the formula Ir₁

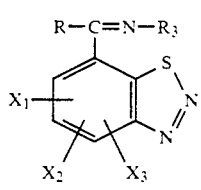
(Ir₁)

are prepared by reacting compounds of the formulae Ic or Id with compounds of the formula H₂N—R₃ in aprotic or protic solvents with or without an addition of an inorganic or organic acid, for example glacial acetic acid, p-toluenesulfonic acid or sulfuric acid, and also with or without carrying out an azeotropic distillation for removing the water of reaction which has formed, or by adsorption of the latter on a molecular sieve at $0°$ to $150°$ C.; and 11.2 Compounds of the formula Ir₂

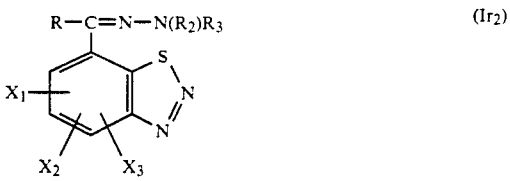
(Ir₂)

are prepared by reacting compounds of the formula Ic or Id with compounds of the formula H₂N—N(R₂)₃ in aprotic or protic solvents with or without an addition of an inorganic or organic acid, for example glacial acetic acid, p-toluenesulfonic acid or sulfuric acid, as well as with or without carrying out an azeotropic distillation for removing the water of reaction which has formed, or by adsorption of the latter on a molecular sieve at $0°$ to $150°$ C.; where R, R₁, R₂ and R₃ as well as X₁, X₂ and X₃ have the meanings given under formula I.

11.3 Compounds of the formula Ir₃

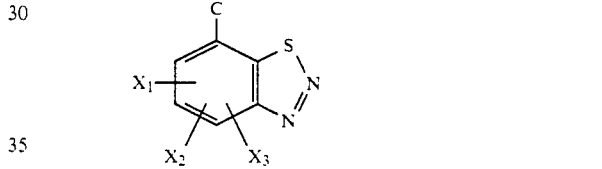
(Ir₃)

are prepared by coupling phenyldiazonium salts U₁—N₂⊕ to phenyl hydrazones of the (Ir₂)' type in aqueous alcoholic solution in a weakly acidic or basic medium at temperatures between $-20°$ and $+30°$ C. pH values $\geq 3$ during the coupling reaction can be established, for example, by adding inert pyridine bases (pyridine, collidine) or alkali metal hydroxides or alkali metal oxides.

12.1 Compounds of the formulae Is₁ and Is₂

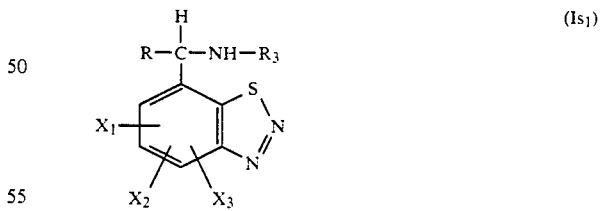
(Is₁)

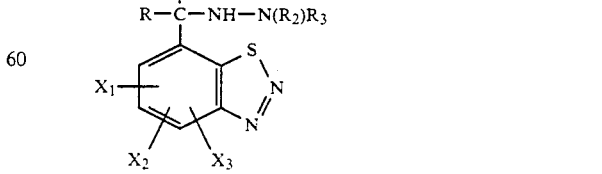
(Is₂)

are prepared either by reducing the compounds of the formulae Ir₁ and Ir₂ respectively, for example by catalytic hydrogenation in the presence of a metal catalyst or by means of a complex hydride, and, in a preferred embodiment, by reacting compounds of the formula

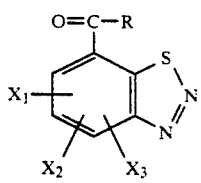

with compounds of the formulae HN(R$_2$)R$_3$ and HN(R$_1$)—N(R$_2$)R$_3$ in the presence of sodium cyanoborohydride in dilute acetic acid at 0° to 120° C.; where R$_1$, R$_2$ and R$_3$ as well as X$_1$, X$_2$ and X$_3$ have the meanings given under formula I; and 13.1 Compounds of the formulae It$_1$ and It$_2$

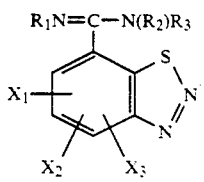 (It$_1$)

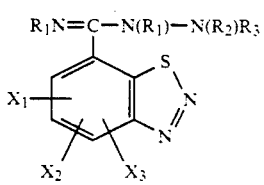 (It$_2$)

are prepared:

13.1.1 by reacting compounds of the formula V with compounds of the formula ROH in the presence of an anhydrous acid, for example gaseous HCl, at −20° to 90° C., to give compounds of the formula IX

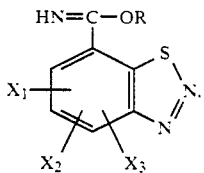 (IX)

and subsequently reacting the compounds of the formula IX with compounds of the formulae HN(R$_2$)R$_3$ and HN(R$_1$)—N(R$_2$)R$_3$ in inert solvents at −20° to 120° C.; or 13.1.2 by reacting compounds of the formula X

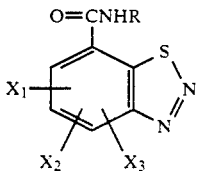 (X)

with PCl$_5$ or CCl$_4$ in the presence of P(phenyl)$_3$ and CH$_3$CN in inert solvents, for example toluene or acetonitrile, at −50° to 150° C., preferably −20° to 90° C., to give compounds of the formula XI

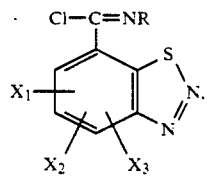 (XI)

and subsequently reacting compounds of the formula XI with compounds of the formulae HN(R$_2$)R$_3$ and HN(R$_1$)—N(R$_2$)R$_3$ in inert solvents at −20° to 120° C.; where R, R$_1$, R$_2$ and R$_3$ as well as X$_1$, X$_2$ and X$_3$ have the meanings given under formula I;

14.1 Compounds of the formulae Iu$_1$, Iu$_2$ and Iu$_3$

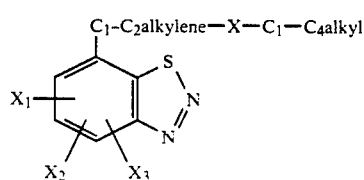 (Iu$_1$)

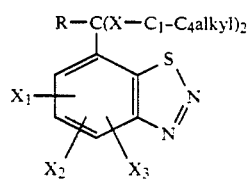 (Iu$_2$)

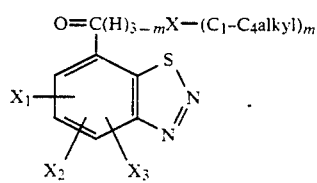 (Iu$_3$)

are prepared by reacting compounds of the formulae Ie, If, Ig, Ik$_1$, Ik$_2$ and Ik$_3$

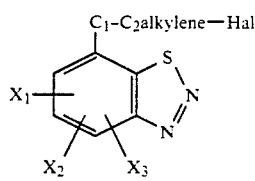 (Ie)

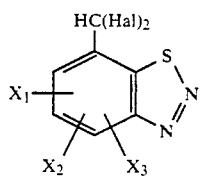 (If)

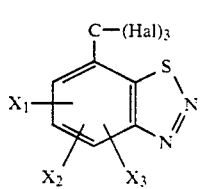 (Ig)

-continued

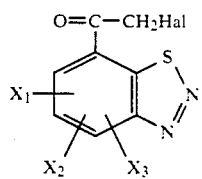
(Ik₁)

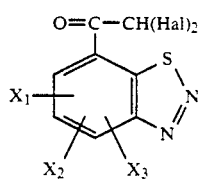
(Ik₂)

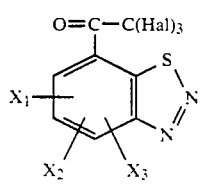
(Ik₃)

with compounds of the formula H—X—C₁-C₄alkyl in inert solvents with or without an addition of a base, for example potassium carbonate, sodium hydride or an alkali metal salt of H—X—C₁-C₄alkyl, in an inert, preferably dipolar, aprotic solvent, for example dimethylformamide or dimethyl sulfoxide, at −20° to 150° C.; or 14.2 Compounds of the formula Iu₂ are prepared by reacting compounds of the formula Ic and Id with an alcohol of the formula HX—C₁-C₄alkyl in the presence of an acid catalyst, for example sulfuric acid, p-toluenesulfonic acid or oxalic acid, with or without an addition of a Lewis acid, for example AlCl₃ or boron trifluoride etherate, with azeotropic distillation or by means of a molecular sieve in inert solvents, for example toluene, dioxane or tetrahydrofuran, or in an excess of compounds of the formula HX—C₁-C₄alkyl at 0° to 180° C.; or 14.3 Compounds of the formula Iu₃ in which X is oxygen are prepared by reacting compounds of the formula IX or the hydrohalides thereof with at least 2 equivalents of a compound of the formula HX—C₁-C₄alkyl with or without an addition of a base, for example an alkali metal salt of compounds of the formula HX—C₁-C₄alkyl, with or without inert solvents at −30° to 80° C.; where X, X₁, X₂ and X₃ have the meanings given under formula I; and 15. Compounds of the formulae Iv₁ and Iv₂

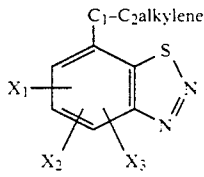
(Iv₁)

-continued

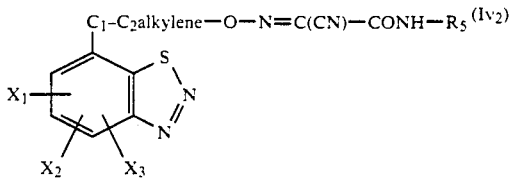
(Iv₂)

are prepared by reacting compounds of the formula Ie with compounds of the formulae M—O—N=C(R₁)R₂ or M—O—N=C(CN)CONH—R₅ in inert solvents and, in the event that M is hydrogen, in the presence of a base, for example alkali metal carbonate, sodium hydride or a tert-amine, for example pyridine, at −20° to 140° C.; where M is hydrogen or an alkali metal atom and R₁, R₂ and R₅ as well as X₁, X₂ and X₃ have the meanings given under formula I; and 16. Compounds of the formula Iw

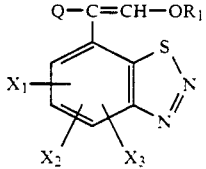
(Iw)

are prepared:

16.1 by reacting compounds of the formula XVI

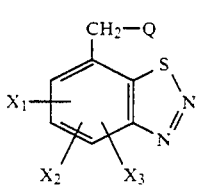
(XVI)

with C₁-C₄alkyl formate or C₁-C₄alkyl orthoformate in the presence of a base, for example sodium alcoholate or sodium hydride, in inert solvents, for example ether, tetrahydrofuran or toluene, at −10° to 120° C. and 16.2 subsequently allowing the resulting compounds of the formula Iw in which R₁ is hydrogen to react with compounds of the formula R₁Hal where R₁ is C₁-C₂alkyl, at 0° to 80° C. with the addition of a base and a dipolar aprotic solvent, for example dimethylformamide; where Q, R₁, X₁, X₂ and X₃ have the meanings given under formula I.

17. Compounds of the formula Ix₁ and Ix₂

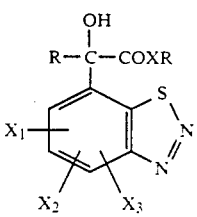
(Ix₁)

-continued

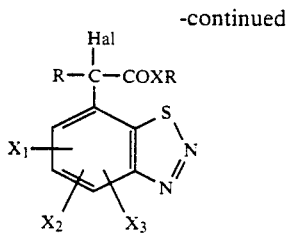

are prepared by hydrolytic reaction of compounds of the formulae $In_1$, $In_2$, $In_3$ and $In_4$ with aqueous mineral acids or by basic hydrolysis of compounds of the formula Ih or Ii with alkali metal hydroxide with or without an addition of inert solvents, for example tetrahydrofuran, at $-10°$ to $180°$ C., preferably $0°$ to $100°$ C.; where Hal is halogen and X, R, $X_1$, $X_2$ and $X_3$ have the meanings given under formula I. This gives the free acids (R=hydrogen). If desired, these acids can be esterified with an alcohol RXH in the presence of water-eliminating catalysts, for example boron trifluoride etherate, at $0°$ to $160°$ C., with or without solvent; and 18. Compounds of the formula Iy

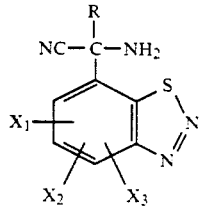

are prepared:

18.1 by reacting compounds of the formula Ic or Id with alkali metal cyanide and ammonia in the presence of ammonium halide at $-20°$ to $80°$ C. with or without an addition of inert solvents, or 18.2 by reacting compounds of the formula $In_1$, $In_2$, $In_3$ or $In_4$ with ammonia in the presence of ammonium halide at $-20°$ to $80°$ C. with or without an addition of inert solvents; where R, $X_1$, $X_2$ and $X_3$ have the meanings given under formula I; and 19. Compounds of the formula Iz

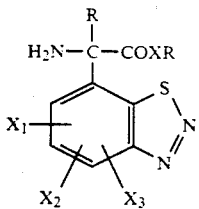

are prepared by hydrolysing compounds of the formula Ig with aqueous mineral acid, for example HCl, at $-20°$ to $130°$ C.; where R, X, $X_1$, $X_2$ and $X_3$ have the meanings given under formula I.

Surprisingly, it has now been found that the use of the compounds of the formula I according to the invention prevents the attack of plants by harmful microorganisms and thus prevents damage to the plants caused by such attacks. It is characteristic of the active ingredients according to the invention that protection of the plants can be achieved by direct action on the destructive microorganisms by means of foliar application or application via the soil as well as by activation and stimulation of the plant's defense system (immunisation). The great advantage of the compounds of the formula I is the fact that maintaining good health of the plants which have been treated with these substances can also be guaranteed on their own account without using further microbicidal substances during the vegetation period. Accordingly, adverse side-effects, as can occur given direct control of parasites using chemical substances, for example on the one hand by inflicting damage on the useful plants (phytotoxicity) and, on the other hand, by causing symptoms of resistance in the harmful microorganisms, can be avoided by using the active ingredients according to the invention, which advantageously entails entirely undisturbed growth of the useful plants.

Comprehensive protection of the plants against diseases can be achieved because of the specific mode of action of the compounds of the formula I according to the invention, namely, on the one hand, the possibility of direct control of the plant pathogens and, on the other hand, improvement of the general defence capacity of the plants treated with these active ingredients by immunisation. The use of the active ingredients according to the invention is therefore particularly suited to practical conditions. Moreover, the systemic activity of the compounds of the formula I means that the protective effect also extends to newly-growing parts of the treated plants.

The general crop-protecting activity of the active ingredients according to the invention extends, for example, to phytopathogenic fungi of the following classes: Fungi imperfecti (for example Botrytis, Helminthosporium, Fusarium, Septoria, Cercospora and Alternaria); Basidiomycetes (for example Hemileia, Rhizoctonia, Puccinia); Ascomycetes (for example Venturia, Podosphaera, Erysiphe, Monilinia, Uncinula).

Moreover, the active ingredients can be used particularly advantageously against the following harmful organisms: fungi, for example Oomycetes (for example *Plasmopara viticola, Phytophthora infestans, Peronospora tabacina*, Pseudoperonospora, *Bremia letucae*), Fungi imperfecti (for example *Colletotrichum lagenarium, Pyricularia oryzae, Cercospora nicotinae*), Ascomycetes (for example *Venturia inaequalis*); bacteria, for example Pseudomonas species (*pseudomonas lachrymans, Pseudomonas tomato, Pseudomonas tabaci*); Xanthomonas species (for example *Xanthomonas oryzae, Xanthomonas vesicatoria*); Erwinia (for example *Erwinia amylovora*); and viruses, for example tobacco mosaic virus.

The compounds according to the invention can be used for protecting a variety of useful plants.

Within the scope of the invention, for example the following plant species are suitable for use of the compounds of the formula I according to the invention: cereals (wheat, barley, rye, oats, rice, sorghum and related species); beet (sugar and fodder beet); pomaceous fruit, stone fruit and soft fruit (apples, pears, plums, peaches, almonds, cherries, strawberries, raspberries and blackberries); legumes (beans, lentils, peas, soybeans); oil crops (rape seed oil, mustard, poppies, olives, sunflowers, coconut, castor cacao, peanuts); cucurbits (pumpkin, cucumbers, melons); fibre plants (cotton, flax, hemp, jute); citrus fruit (oranges, lemons, grapefruit, tangerines); various vegetables (spinach, lettuce, asparagus, cabbage species, carrots, onions, tomatoes, potatoes, sweet peppers); Lauraceae (avocado, Cinnamonum, camphor) or plants such as maize, tobacco, nuts, coffee, sugar cane, tea, grape vine, hops, Musaceae and latex plants, as well as ornamentals (flowers, shrubs, deciduous trees and conifers). This list does not imply any limitation.

The following plants can be regarded as particularly suitable target crops for the use of the method according to the invention: cucumber, tobacco, grape vine, rice, pepper, potatoes, tomatoes, wheat, barley, pears and apples.

The microbicidal compositions for protecting plants against diseases which are employed within the scope of the invention and comprise the compounds of the formula I as active ingredients are to be considered as part of the invention.

Active ingredients of the formula I are customarily used in the form of combinations and can be applied to the plant or its environment simultaneously or in succession with other active ingredients. These other active ingredients can be fertilisers, trace element supplements, or other preparations which have an effect on plant growth. However, they can also be selective herbicides, insecticides, fungicides, bactericides, nematicides, molluscicides or mixtures of several of these preparations, if desired together with other carriers, surfactants or application-enhancing additives conventionally used in the art of formulation.

Suitable carriers and additives can be solid or liquid and correspond to the substances expedient in the art of formulation, for example natural or regenerated mineral substances, solvents, dispersants, wetting agents, adhesives, thickeners, binders or fertilisers.

One method of applying an active ingredient of the formula I, or an agrochemical composition comprising at least one of these active ingredients, is application to the plant (foliar application). However, the active ingredients of the formula I can also reach the plant from the soil via the root system (soil application), by soaking the locus of the plant with a liquid preparation or incorporating the substances into the soil in solid form, for example in the form of granules. However, the compounds of the formula I can also be applied to seed kernels (coating) either by soaking the seeds with a liquid preparation of the active ingredient or by applying a layer of a solid preparation (application by seed-dressing). Moreover, other types of application are possible in specific cases, for example the targeted treatment of the stalks of the plants, or of the buds.

The compounds of the formula I are employed in unaltered form, or, preferably, together with the auxiliaries conventionally used in the art of formulation. For this purpose, they are processed in a known manner to give, for example, emulsion concentrates, spreadable pastes, directly sprayable or dilutable solutions, dilute emulsions, wettable powders, soluble powders, dusts, granules, or encapsulations, for example in polymeric substances. The application methods such as spraying, atomising, dusting, scattering, brushing on or pouring, as well as the type of composition are selected to suit the intended aims and the prevailing circumstances. Favourable rates of application are generally 50 g to 5 kg of active substances (AS) per ha; preferably 100 g to 2 kg AS/ha, in particular 100 g to 600 g AS/ha.

The formulations, i.e. the compositions, preparations or combinations comprising the active ingredient of the formula I and, if appropriate, a solid or liquid additive, are prepared by intimately mixing and/or grinding the active ingredients together with extenders, for example with solvents, solid carriers and, if appropriate, surface-active compounds (surfactants).

The following are suitable as solvents: aromatic hydrocarbons, preferably the fractions $C_8$ to $C_{12}$, for example xylene mixtures or substituted naphthalenes, phthalic esters such as dibutyl phthalate or dioctyl phthalate, aliphatic hydrocarbons such as cyclohexane or paraffins, alcohols and glycols as well as the ethers and esters thereof such as ethanol, ethylene glycol, ethylene glycol monomethyl ether or ethylene glycol monoethyl ether, ketones such as cyclohexanone, strongly polar solvents such as N-methyl-2-pyrrolidone, dimethyl sulfoxide or dimethylformamide; and epoxidised or unepoxidised vegetable oils such as epoxidised coconut oil or soya oil; or water.

Solid carriers which are generally used, for example for dusts and dispersible powders, are ground natural minerals such as calcite, talc, kaolin, montmorillonite or attapulgite. To improve the physical properties, it is also possible to add highly-disperse silicas or highly-disperse absorptive polymers. Granular, adsorptive granule carriers which are suitable are porous types, for example pumice, brick grit, sepiolite or bentonite, and suitable non-sorptive carrier materials are, for example, calcite or sand. In addition, a large number of pregranulated materials of inorganic or organic nature such as, in particular, dolomite or comminuted plant residues, can be used.

Suitable surface-active compounds are non-ionic, cationic and/or anionic surfactants having good emulsifying, dispersing and wetting properties, depending on the nature of the active ingredient of the formula I to be formulated. Surfactants are also to be understood as meaning mixtures of surfactants.

The cationic surfactants are mainly quaternary ammonium salts which comprise at least one alkyl radical having 8 to 22 C atoms as the N substituent and have lower, halogenated or free alkyl, benzyl or lower hydroxyalkyl radicals as further substituents.

Suitable anionic surfactants can be either so-called water-soluble soaps or water-soluble synthetic surface-active compounds.

Soaps which may be mentioned are the alkali metal salts, alkaline earth metal salts or substituted or unsubstituted ammonium salts of higher fatty acids ($C_{10}$-$C_{22}$), for example the sodium or potassium salts of oleic or stearic acid, or of natural fatty acid mixtures, for example those which can be obtained from coconut oil or tallow oil.

Synthetic surfactants which can be used are, in particular, fatty alcohol sulfonates, fatty alcohol sulfates, sulfonated benzimidazole derivatives or alkyl sulfonates. The fatty alcohol sulfonates or fatty alcohol sulfates are generally in the form of alkali metal salts, alkaline earth metal salts or substituted or unsubstituted ammonium salts, and have an alkyl radical having 8 to 22 C atoms.

Suitable non-ionic surfactants are mainly polyglycol ether derivatives of aliphatic or cycloaliphatic alcohols, saturated or unsaturated fatty acids and alkylphenols which can have 3 to 30 glycol ether groups and 8 to 20 carbon atoms in the (aliphatic) hydrocarbon radical and 6 to 18 carbon atoms in the alkyl radical of the alkyl phenols.

The compositions can also comprise further additives such as stabilisers, defoamers, viscosity regulators, binders and adhesives as well as fertilisers or other active ingredients for achieving specific effects.

The agrochemical preparations generally comprise 0.1 to 99% by weight, in particular 0.1 to 95% by weight, of active ingredient of the formula I, 99.9 to 1% by weight, in particular 99.8 to 5% by weight, of a solid or liquid additive, and 0 to 25% by weight, in particular 0.1 to 25% by weight, of a surfactant.

The examples which follow are intended to illustrate the invention in greater detail without implying any limitation of the latter.

1. PREPARATION EXAMPLES

EXAMPLE 1.1

Preparation of 7-methylsulfonyloxymethylbenzo-1,2,3-thiadiazole (Comp. No. 1.20)

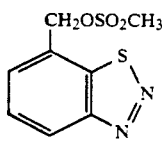

To a solution of 3.32 g of 7-hydroxymethylbenzo-1,2,3-thiadiazole, 3.1 ml of triethylamine and 0.2 g of 4-dimethylaminopyridine in 50 ml of methylene chloride there is added dropwise with cooling at −5° to 0° C. a solution of 2.23 g of methanesulfonyl chloride in 15 ml of dichloromethane, and the mixture is stirred for 2 hours at room temperature. The reaction mixture is then treated with ice-water and extracted several times using dichloromethane. The combined extracts are washed with water, dried and evaporated. Chromatographic purification on silica gel ($CH_2Cl_2$) gives the title compound as a viscous resin.

EXAMPLE 1.2

Preparation of benzo-1,2,3-thiadiazole-7-carbaldehyde (Comp. No. 1.4)

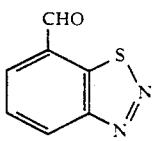

a) 99 g of benzo-1,2,3-thiadiazole-7-carboxylic acid chloride are dissolved in 1.2 l of ethyl acetate, the mixture is treated at 0°–5° C. with a solution of 58.7 g of 2,6-lutidine in 200 ml of tetrahydrofuran as well as 33 g of palladium/charcoal catalyst (5% Pd), and hydrogenated under low pressure ($10^4$ Pa) with a further addition of a total of 57 g of palladium/charcoal catalyst and 500 ml of tetrahydrofuran in 5 portions. The catalyst is subsequently removed by filtration and washed with tetrahydrofuran, and the filtrate is evaporated. The residue is purified on silica gel ($CH_2Cl_2$) and gives the title compound of m.p. 134°–136° C.

b) To a solution of 16.6 g of 7-hydroxymethylbenzo-1,2,3-thiadiazole in 100 ml of chloroform there are introduced with stirring at room temperature 35 g of manganese dioxide, during which process the internal temperature rises briefly to 31° C. When the temperature has dropped again to 25° C., the mixture is heated and refluxed overnight. Another 5 g of manganese dioxide are subsequently added, and heating of the mixture is continued until the reaction is complete. The hot mixture is filtered over Hyflo and the filtrate is then evaporated. The residue is digested in a little hexane and then filtered, which gives 15 g (91.4%) of the title compound of m.p. 134°–136° C.

EXAMPLE 1.3

Preparation of 7-trichloromethylbenzo-1,2,3-thiadiazole (Comp. No. 1.2)

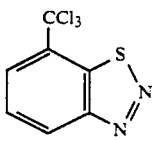

26 g of phosphorus pentachloride are introduced in portions to 9.0 g of 7-carboxybenzo-1,2,3-thiadiazole and 10.7 g of benzenephosphonic acid dichloride under a nitrogen atmosphere and with stirring. The mixture (which exists in solid form) is then heated to 160° C., during which process melting starts at approx. 100° C. After the mixture has been stirred for 16 hours at 160° C., it is cooled, carefully poured onto ice, and the mixture is rendered alkaline using solid sodium carbonate. It is then extracted several times using ethyl acetate, the extracts are washed with water and filtered over Hyflo, and the filtrate is evaporated. Purification on silica gel (hexane with an increasing addition of ethyl acetate up to a ratio of 8:2) gives white crystals of m.p. 67°–69° C.

EXAMPLE 1

Preparation of 7-dichloromethylbenzo-1,2,3-thiadiazole (Comp. No 1.1)

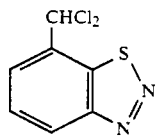

8.7 ml of thionyl chloride are initially introduced, and 0.5 ml of triethylamine are added with cooling, 6.6 g of benzo-1,2,3-thiadiazole-7-carbaldehyde are then introduced in portions at 15°–20° C., and the mixture is subsequently heated for 1 hour at 45° C. and then for a further 4 hours at 95° C., during which process slight evolution of gas can be observed. The clear solution which has formed is subsequently evaporated, the residue is taken up in methylene chloride, and the mixture is washed with ice-water. The organic phase is dried over sodium sulfate and evaporated. The residue is recrystallised from ethyl acetate/hexane, giving the title compound of m.p. 131°–133° C.

EXAMPLE 1.5

Preparation of 7-chloromethylbenzo-1,2,3-thiadiazole (intermediate)

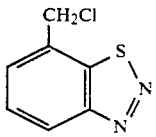

199.2 g of the compound of Example 1.15 are dissolved in 150 ml of methylene chloride and 150 ml of pyridine at 5° C., introduced into a reaction vessel, and treated at 5°–10° C. in the course of ¾ hours with a solution of 120 ml of thionyl chloride in 200 ml of methylene chloride, with cooling. Stirring is then continued at room temperature overnight, the suspension is poured into ice-water, and the mixture is extracted using methylene chloride. The extracts are washed with ice-water, dried over sodium sulfate and filtered, and the filtrate is evaporated. The resulting title compound melts at 78°–80° C.

EXAMPLE 1.6

Preparation of 7-acetylbenzo-1,2,3-thiadiazole (Comp. No. 1.5)

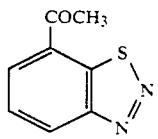

0.59 g of magnesium turnings in 3 ml of diethyl ether are activated with 1 drop of bromine, and a solution of 1.5 ml of methyl iodide in 5.5 ml of diethyl ether is added dropwise with stirring. When the exothermic reaction has subsided, the mixture is heated and kept for a further 1.5 hours at bath temperature 55° C. The resulting solution is added dropwise under a nitrogen atmosphere and with stirring at −10° C. to the initially introduced solution of 4.9 g of N-methyl-N-methoxybenzo-1,2,3-thiadiazole-7-carboxamide in 150 ml of absolute tetrahydrofuran. After stirring has been continued for 1 hour at −10° C., the mixture is heated and refluxed at bath temperature 75° C. for 6 hours. The reaction mixture is then cooled, poured into ice-water, acidified with 2N hydrochloric acid and extracted several times using ethyl acetate. The extracts are washed with water, dried over sodium sulfate and evaporated. The residue is purified on silica gel (CHCl$_3$), giving the title compound of m.p. 126°–127° C.

EXAMPLE 1.7

Preparation of 7-carboxymethylbenzo-1,2,3-thiadiazole (Comp. No. 1.39)

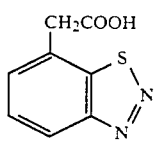

1.9 g of 7-cyanobenzo-1,2,3-thiadiazole are heated overnight in 80 ml of concentrated hydrochloric acid. The mixture is then evaporated and treated with a little cold water, and the solid which has formed is filtered off and washed with water. The residue is dried, resulting in 1.7 g of the title compound of m.p. 148°–150° C.

EXAMPLE 1.8

Preparation of 3-[benzo-1,2,3-thiadiazol-7-yl]acrylic acid (Comp. No. 1.98)

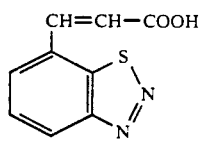

A mixture of 1.96 g of benzo-1,2,3-thiadiazole-7-carbaldehyde, 1.24 g of malonic acid and 6 ml of pyridine are heated for 26 hours at 120° C., with 2 further additions of 0.6 g portions of malonic acid after 4 and 7 hours. The mixture is then cooled, poured into ice-water and acidified with concentrated hydrochloric acid. The precipitate which has formed is filtered off and dissolved in dilute sodium hydroxide solution, the mixture is washed three times with methylene chloride, and the aqueous phase is subsequently acidified once more, using hydrochloric acid. The precipitate obtained is filtered off, washed with water and dried in vacuo, resulting in 11 g of the title compound of m.p. 199°–202° C.

EXAMPLE 1.9

Preparation of 7-cyanomethylbenzo-1,2,3-thiadiazole (Comp. No. 1.38)

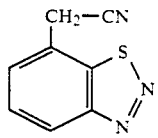

18.4 g of 7-chloromethylbenzo-1,2,3-thiadiazole are dissolved in 50 ml of chloroform, 0.5 g of tetrabutylammonium iodide are added, the mixture is heated to 50°–55° C. and treated dropwise in the course of 0.5 hours with a solution of 5.6 g of sodium cyanide in 20 ml of water, with stirring. Heating is continued overnight at the same temperature, on the following day the mixture is cooled, treated with water and extracted several times using dichloromethane. The extracts are washed with water, dried over sodium sulfate and filtered over Hyflo, and the filtrate is evaporated. The residue is purified on silica gel (hexane/ethyl acetate) resulting in the title compound of m.p. 78°–80° C.

EXAMPLE 1.10

Preparation of ethyl 3-[benzo-1,2,3-thiadiazolyl]-3-oxo-2,2-diethoxypropionate (Comp. No. 1.64)

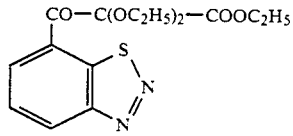

71.5 g of benzo-1,2,3-thiadiazole-7-carboxylic acid chloride and 88.1 g of tetraethoxyethylene are refluxed for 17 hours in 180 ml of toluene. The mixture is then cooled, washed with sodium bicarbonate solution and water, dried over sodium sulfate and evaporated. The solid residue is dissolved in hot tetrahydrofuran and precipitated with hexane, with stirring. This results in 61.5 g of the title compound of m.p. 123°–125° C.

EXAMPLE 1.11

Preparation of 7-trifluoromethylbenzo-1,2,3-thiadiazole

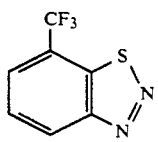

38.8 g of 3,5-diamino-3-benzylthiobenzotrifluoride in 100 ml of dioxane are added dropwise with vigorous stirring at 0° C. with cooling to 195 ml of 5N hydrochloric acid. The mixture is subsequently cooled to −15° C., and, below the liquid level, treated dropwise with 18.6 g of sodium nitrite in 150 ml of water. The red solution is subsequently stirred for 6 hours at −5° C. and finally poured into hypophosphorous acid (71 ml) which has been cooled to −10° C., with stirring. The mixture is allowed to cool to room temperature overnight with continued stirring and on the following day the mixture is extracted several times using methylene chloride, and the extracts are washed with water, dried over sodium sulfate and then evaporated. The oily residue is freed from benzyl chloride by repeated distillation using a bulb tube at 80° C./7.8 Pa.

EXAMPLE 1.12

Preparation of 3,5-diamino-2-benzylthiobenzotrifluoride (intermediate)

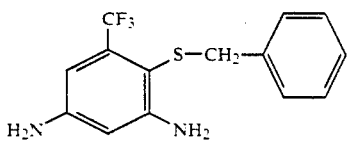

3 g of 2-benzylthio-3,5-dinitrobenzotrifluoride in 30 ml of tetrahydrofuran are hydrogenated in a glass hydrogenation apparatus for 22 hours at room temperature, using a total of 3 g of Raney nickel. For working up, the catalyst is removed by filtration and washed with tetrahydrofuran, the filtrate is evaporated, and the residue is directly processed as crude product (brownish liquid).

EXAMPLE 1.13

Preparation of 2-benzylthio-3,5-dinitrobenzotrifluoride (intermediate)

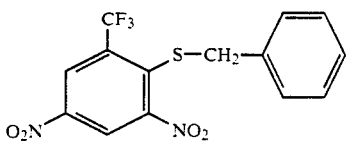

67.6 g of 2-chloro-3,5-dinitrobenzotrifluoride are dissolved in 150 ml of N,N-dimethylformamide (DMF) and the mixture is treated with 35.9 g of solid potassium carbonate, treated dropwise with 31 g of benzylmercaptan in 200 ml of DMF with stirring at 0° C., and subsequently stirred for a further 16 hours at room temperature, while cooling.

The reaction mixture is then treated with ice-water and extracted several times using methylene chloride. The extracts are washed with water, dried and evaporated. The residue is digested with hexane with heating, and the mixture is filtered. This gives yellow crystals of m.p. 93°–95° C.

EXAMPLE 1.14

Preparation of ethyl benzo-1,2,3-thiadiazole-7-carboximidate hydrochloride (intermediate)

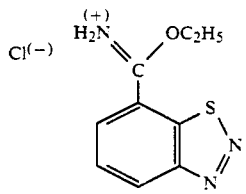

7.2 g of 7-cyanobenzo-1,2,3-thiadiazole are dissolved at 45° C. in 60 ml of absolute ethanol and 20 ml of tetrahydrofuran, and the solution is cooled to 0° C. and saturated with gaseous hydrochloric acid in the course of 1 hour at 0° C. to 15° C., with the exclusion of moisture. The reaction mixture is then stored for 24 hours in the refrigerator, treated with 70 ml of absolute diethyl ether and allowed to stand for another 4 days in the refrigerator. The solid is then filtered off, washed with diethyl ether and dried. This gives 9.4 g of compound 5.2 in the form of beige crystals of m.p. 270°–272° C.

EXAMPLE 1.15

Preparation of 7-hydroxymethylbenzo-1,2,3-thiadiazole (intermediate)

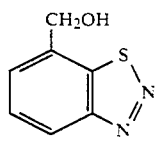

To a suspension of 54 g of carboxybenzo-1,2,3-thiadiazole in 420 ml of tetrahydrofuran there are added dropwise under a nitrogen atmosphere with stirring at room temperature 110 ml of triethyl borate, the mixture is stirred for a further hour and subsequently treated dropwise with 45.6 ml of boranedimethyl sulfide complex in 60 ml of tetrahydrofuran, with gentle cooling, during which process gas is evolved vigorously. The mixture is stirred overnight and allowed to stand at room temperature and then cooled down to 5°–10° C. and treated dropwise with 200 ml of methanol with stirring and vigorous cooling, during which process gas is again evolved vigorously. The mixture is subsequently evaporated in vacuo, a further 300 ml of methanol are added, and the mixture is re-evaporated. The residue is purified on silica gel (solvent: ethyl acetate/hexane), and the product obtained is recrystallised from ethyl acetate/hexane. The title compound obtained melts at 79°–81° C.

EXAMPLE 1.16

Preparation of 6-chloro-7-hydroxymethylbenzo-1,2,3-thiadiazole (intermediate)

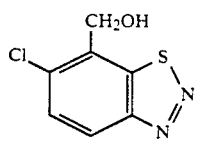

To a suspension of 4.5 g of sodium borohydride in 30 ml of water and 70 ml of tetrahydrofuran there are added dropwise with stirring and heating to 40°–50° C. in the course of half an hour a solution of 1.9 g of 6-chloro-7-carbomethoxybenzo-1,2,3-thiadiazole in 30 ml of tetrahydrofuran (dissolved under hot conditions). Heating of the mixture is continued until the reaction is complete, and the mixture is then cooled to $-20°$ to $-30°$ C. using a $CO_2$ cooling bath and treated dropwise with 15 ml of acetone, during which process gas is evolved vigorously. The reaction mixture is subsequently brought to pH 3 using 15% hydrochloric acid, with further vigorous cooling at $-20°$ to $-10°$ C. (evolution of gas), and stirring is continued overnight. Most of the tetrahydrofuran is then evaporated on a rotary evaporator, and the residue is extracted using ethyl acetate. The extracts are washed with water, dried over sodium sulfate and evaporated. The residue gives the title compound of m.p. 138°–140° C.

EXAMPLE 1.17

Preparation of 2-(benzo-1,2,3-thiadiazolyl)-2-hydroxyiminoacetonitrile (Comp. No. 1.127)

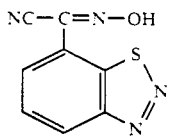

A suspension of 0.36 g of potassium tert-butylate in 5 ml of absolute diethyl ether is treated dropwise at $-5°$ C. in the course of 10 minutes with a solution of 0.5 g of 7-cyanomethylbenzo-1,2,3-thiadiazole and 0.43 ml of isoamyl nitrite in 10 ml of absolute tetrahydrofuran, and stirred at room temperature for a total of 48 hours, with three additions of 0.43 ml portions of isoamyl nitrite being added at intervals of 16, a further 16 and 8 hours. The mixture is then diluted with ice-water, acidified with 1N hydrochloric acid and extracted with ethyl acetate. The extracts are washed with water, dried over sodium sulfate and evaporated. Chromatography of the residue on silica gel (ethyl acetate/hexane 1:2) gives the title compound of m.p. 249°–253° C.

EXAMPLE 1.18

Preparation of 7-(1,1,1-trichloro-2-hydroxy(ethyl))benzo-1,2,3-thiadiazole (Comp. No. 1.108)

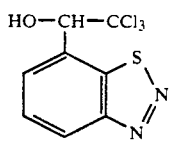

A mixture of 5.8 g of trichloroacetic acid and 2.6 g of 7-formylbenzo-1,2,3-thiadiazole in 20 ml of hexamethylphosphoric triamide is heated for 4 hours at 70° C., during which process the solid dissolves rapidly, with evolution of $CO_2$. The mixture is then cooled, poured into ice-water and extracted with ethyl acetate. The extracts are washed with water, dried and evaporated. The residue is recrystallised from ethyl acetate/hexane, resulting the title compound of m.p. 163°–165° C.

EXAMPLE 1.19

Preparation of 7-aminomethylbenzo-1,2,3-thiadiazole (Comp. No. 1.110)

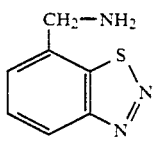

In a hydrogenation vessel, a solution of 14.5 g of 7-cyanobenzo-1,2,3-thiadiazole in 150 ml of methanol is treated with 4.4 g of Raney nickel and with 15 g of liquid nitrogen. Hydrogen is subsequently injected, the vessel is heated, and the mixture is hydrogenated at 60° C. and constant hydrogen pressure of $10^7$ Pa until hydrogen is no longer taken up. The mixture is then cooled, the catalyst is removed by filtration, the filtrate is evaporated and chromatographed on silica gel (hexane/ethyl acetate 2:1), resulting in the title compound of m.p. 136°–139° C.).

EXAMPLE 1.20

Preparation of 7-trichloroacetylbenzo-1,2,3-thiadiazole (Comp. No. 1.107)

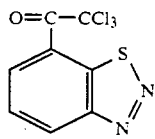

A solution of 2.8 g of 7-(1,1,1-trichloro-2-hydroxyeth-2-yl)benzo-1,2,3-thiadiazole in 30 ml of chloroform is treated with 5 g of manganese dioxide and refluxed for 16 hours, with stirring. A further 5 and 3 g of manganese dioxide are added at intervals of 16 hours and 8 hours, respectively. After a total of 40 hours, the mixture is cooled and filtered twice through Hyflo, the filtrate is evaporated and purified using silica gel (hexane/ethyl acetate 7:3), giving the title compound of refractive index $n_D^{26} = 1.6178$.

EXAMPLE 1.21

Preparation of 7-acetylthiomethylbenzo-1,2,3-thiadiazole (Comp. 1.113)

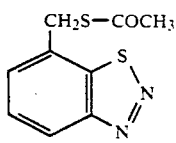

A solution of 2.2 g of potassium thioacetate in 20 ml of absolute dimethyl sulfoxide, stirred at 20° C., is treated dropwise with stirring with a solution of 2.8 g of 7-chloromethylbenzo-1,2,3-thiadiazole in 10 ml of dimethyl sulfoxide, during which process the internal temperature rises to 37° C. The mixture is subsequently stirred overnight at room temperature and, on the following day, poured into ice-water and extracted using ethyl acetate. The extracts are washed five times with water, dried over sodium sulfate and evaporated. The residue which remains is distilled in vacuo, resulting in an oil of refractive index $n_D^{27} = 1.6478$.

EXAMPLE 1.22

Preparation of 7-dimethoxymethylbenzo-1,2,3-thiadiazole (Comp. No. 1.12)

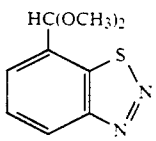

A solution of 3.3 g of 7-formylbenzo-1,2,3-thiadiazole in 50 ml of methanol and 0.2 g of p-toluenesulfonic acid is refluxed for 6 hours in a Soxhlet apparatus charged with a molecular sieve $A_4$. The mixture is then cooled, rendered basic using solid potassium carbonate, filtered through Hyflo and evaporated. The residue is purified on silica gel using hexane/ethyl acetate (1:1), resulting in the title compound of refractive index $n_D^{21} = 1.5750$.

EXAMPLE 1.23

Preparation of benzo-1,2,3-thiadiazole-7-N-methoxyhydroxamic acid (Comp. No. 1.112)

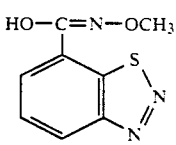

A suspension of 2.4 g of O-methylhydroxylamine hydrochloride, 4.5 g of potassium carbonate and 20 ml of dichloromethane, stirred at $-5°$ C., is treated dropwise with cooling and stirring with a solution of 4.96 g of benzo-1,2,3-thiadiazole-7-carboxylic acid chloride in 25 ml of dichloromethane. The mixture is stirred overnight at room temperature and filtered, the filtrate is evaporated, and the residue is washed on silica gel (ethyl acetate/tetrahydrofuran 1:1). This gives the title compound of m.p. 188°–190° C.

EXAMPLE 1.24

Preparation of 7-methoxymethylbenzo-1,2,3-thiadiazole (Comp. No. 1.7)

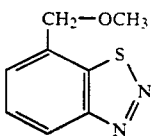

1.4 g of sodium hydride (50% dispersion in oil) in 15 ml of absolute dimethyl sulfoxide are introduced into a reaction vessel, and a solution of 4.15 g of 7-hydroxymethylbenzo-1,2,3-thiadiazole in 15 ml of tetrahydrofuran is added dropwise at 0°–5° C. under a nitrogen atmosphere and with stirring, during which process hydrogen is evolved. After 20 minutes of stirring at 10° C., the mixture is cooled down to 0°–5° C., and a solution of 4 g of methyl iodide in 15 ml of tetrahydrofuran is added dropwise. Stirring is continued for another hour at room temperature, and the mixture is cooled, treated with ice-water, neutralised with dilute hydrochloric acid and extracted with ethyl acetate. The extracts are washed with water, dried over sodium sulfate and evaporated, and the residue is dried in a high vacuum, resulting in the title compound in the form of a yellow oil, $n_D^{27} = 1.5912$.

EXAMPLE 1.25

Preparation of 7-oximinobenzo-1,2,3-thiadiazole (Comp. No. 1.65)

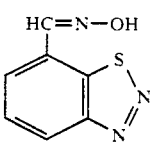

A solution of 4.9 g of 7-formylbenzo-1,2,3-thiadiazole in 70 ml of absolute methanol is treated with 2.1 g of hydroxylamine hydrochloride and 2.4 g of sodium acetate, and the mixture is maintained at 70° C. for 6 hours. Most of the solvent is then evaporated in vacuo, the residue is treated with ice-water, and the precipitate is filtered off, washed with water and dried, resulting in the title compound of m.p. 230°–231° C. (decomp.).

EXAMPLE 1.26

Preparation of 7-methoxyiminobenzo-1,2,3-thiadiazole (Comp. No. 1.66)

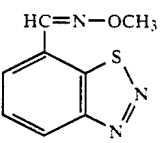

A suspension of 0.92 g of sodium hydride (50% dispersion in oil) in 10 ml of dimethyl sulfoxide and 10 ml of tetrahydrofuran is treated dropwise under a nitrogen atmosphere and with stirring at 0°–10° C. with a solution of 3.0 g of 7-oximinobenzo-1,2,3-thiadiazole in 10 ml of tetrahydrofuran and, after stirring for 0.5 hours at 15°–20° C., treated with 2.7 g of methyl iodide in 10 ml of tetrahydrofuran. After stirring for 5 hours at room temperature, the mixture is treated with ice-water and extracted with methylene chloride, and the extracts are washed with water and dried. The residue which remains after evaporation is digested with hexane, resulting in pale yellow crystals of m.p. 121°–123° C.

EXAMPLE 1.27

Preparation of 7-(3-trifluoromethylphenylimino)benzo-1,2,3-thiadiazole (Comp. No. 1.79)

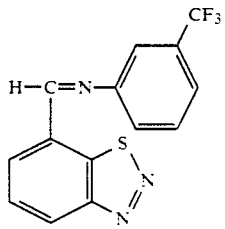

A solution of 2.46 g of 7-formylbenzo-1,2,3-thiadiazole and 2.41 g of 3-aminobenzotrifluoride is stirred for 16 hours at room temperature with a spatulatipful of p-toluenesulfonic acid and approx. 5 g of molecular sieve A4 in 50 ml of toluene. The mixture is then filtered and the filtrate is evaporated, and the residue is washed with hexane and dried, resulting in the title compound of m.p. 120°–122° C.

EXAMPLE 1.28

Preparation of the 2,4,6-trichlorophenylhydrazone of benzo-1,2,3-thiadiazole-7-carbaldehyde (Comp. No. 1.89)

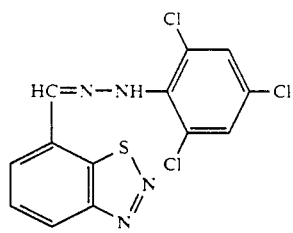

2.11 g of 2,4,6-trichlorophenylhydrazine is dissolved under hot conditions in 30 ml of methanol and 20 ml of tetrahydrofuran, the mixture is cooled to 40° C. and, together with a solution of 2.46 g of benzo-1,2,3-thiadiazole-7-carbaldehyde, poured into 10 ml of methanol, with stirring. After stirring for 4 hours at room temperature, 8 ml of glacial acetic acid are added, and stirring is continued at 40° C. until the reaction is complete. The mixture is then filtered, washed with methanol and dried, resulting in the title compound as beige solid (m.p. >250° C.).

EXAMPLE 1.29

Benzo-1,2,3-thiadiazole-7-(N-hydroxycarboximid(amide) (Compound 1.106)

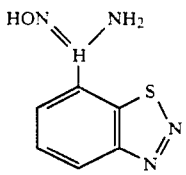

A solution of 5.0 g of 7-cyanobenzo-1,2,3-thiadiazole, introduced into the reaction vessel, and 2.5 g of hydroxylamine hydrochloride in 34 ml of ethanol and 16 ml of water are treated with 6.4 g of potassium carbonate in portions, during which process the internal temperature rises from 24° to 36° C., with gentle evolution of $CO_2$. After stirring for 1½ hours at room temperature, the mixture is refluxed for a further 3 hours, and the suspension which has formed is treated with ice-water, and the solid is filtered off and washed with water and a little diethyl ether. The precipitate corresponds to the title compound of m.p. 209°–211° C.

EXAMPLE 1.30

Preparation of 7-bromoacetylbenzo-1,2,3-thiadiazole (Compound 1.125)

0.9 g of 7-acetylbenzo-1,2,3-thiadiazole is dissolved in 20 ml of chloroform, and 0.88 g of bromine is added dropwise at room temperature. Stirring is then continued for 2 hours at the same temperature, during which process a yellow precipitate forms. This precipitate is filtered off, washed with hexane and dried. The title compound which is thus obtained melts at 155°–157° C.

EXAMPLE 1.31

Preparation of N,N'-diphenyl-C-[benzo-1,2,3-thiadiazol-7'-yl]formazan Compound No. 3.1)

1.65 g of aniline are diazotised at 0° C. using a solution of 1.25 g of sodium nitrite in 2.2 ml of water, in the presence of 4 ml of hydrochloric acid (30%) and 1.8 g of ice. A solution of 4.6 g of benzo-1,2,3-thiadiazole-7-carbaldehydephenylhydrazone in 60 ml of pyridine and 90 ml of ethanol is introduced into the reaction vessel, the solution of the diazonium salt is added dropwise with stirring and cooling at −5° to 0° C., and the reaction mixture is stirred at room temperature for a further 18 hours. The mixture is subsequently concentrated in vacuo and extracted with ethyl acetate. The extracts are washed with water, dried and evaporated. The residue is purified on silica gel (ethyl acetate/hexane 9:1), resulting in the title compound of m.p. 185°–187° C.

TABLE 1

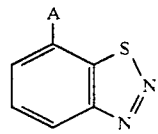

| Comp. No. | A | Physical data |
|---|---|---|
| 1.1 | CHCl₂ | m.p. 131–133° C. |
| 1.2 | CCl₃ | m.p. 67–69° C. |
| 1.3 | CH(Cl)CH₃ | |

TABLE 1-continued

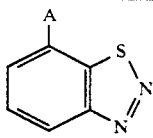

| Comp. No. | A | Physical data |
|---|---|---|
| 1.4 | CBr₃ | |
| 1.5 | H₃C—C(OCH₃)₂ | |
| 1.6 | CH₂OCOCH₃ | m.p. 52–54° C. |
| 1.7 | CH₂OCH₃ | $n_D^{27}$ = 1.5912 |
| 1.8 | CH₂O—CO-cyclopropyl | |
| 1.9 | CH(OH)CH₃ | |
| 1.10 | C(OCH₃)₃ | |
| 1.11 | C(OC₂H₅)₃ | |
| 1.12 | CH(OCH₃)₂ | $n_D^{21}$ = 1.5750 |
| 1.13 | CH(OC₂H₅) | |
| 1.14 | CH[OCH(CH₃)₂]₂ | |
| 1.15 | CH(OC₄H₉-n)₂ | |
| 1.16 | CH(SCH₃)CH₃ | |
| 1.17 | CF₃ | m.p. 80° C./7.8 Pa |
| 1.18 | CH₂SCH₃ | $n_D^{27}$ = 1.6311 |
| 1.19 | CH(S-isoC₃H₇)₂ | |
| 1.20 | CH₂O—SO₂CH₃ | resin |
| 1.21 | CH₂O—SO₂—C₂H₅ | |
| 1.22 | CH₂O—SO₂-cyclohexyl | |
| 1.23 | CH₂O—CO-cyclopropyl | |
| 1.24 | CH(CH₃)O—COCH₃ | |
| 1.25 | CH₂OCO—CH₂CH=CH₂ | |
| 1.26 | CH₂OCO—CH₂—C≡CH | |
| 1.27 | CH₂OCO—CH₂CH=CH—CH₃ | |
| 1.28 | CH₂OCO—CH₂—CH=CH—C₂H₅ | |
| 1.29 | CH₂OCO—C₆H₁₃-n | |
| 1.30 | CH(CH₃)OCO-cyclohexyl | |
| 1.31 | CH₂OCO-penyl | m.p. 73–74° C. |
| 1.32 | CH₂OCO-2-hydroxyphenyl | |
| 1.33 | CH₂OCO—C(Cl)=C(Cl)₂ | m.p. 123–124° C. |
| 1.34 | CH₂O-tosyl | |
| 1.35 | CH₂O—SO₂-4-bromophenyl | |
| 1.36 | CH(CH₃)O—SO₂CH₃ | |
| 1.37 | CH₂O—SO₂C₆H₁₃-n | |
| 1.38 | CH₂CN | m.p. 78–80° C. |
| 1.39 | CH₂COOH | m.p. 148–150° C. |
| 1.40 | CH₂CONH₂ | |
| 1.41 | CH₂COOCH₃ | |
| 1.42 | CH₂COOC₄H₉-tert. | |
| 1.43 | CH₂CO—SCH₃ | |
| 1.44 | CH₂CO—S-phenyl | |
| 1.45 | CH₂COO-phenyl | |
| 1.46 | CH₂COO-2-hydroxyphenyl | |
| 1.47 | CH(CH₃)—COOCH₃ | |
| 1.48 | CH(OH)COOH | |
| 1.49 | CH(OH)—COOCH₃ | |
| 1.50 | CH₂J | |
| 1.51 | CH(CH₃)Br | |
| 1.52 | CH(OH)CN | |
| 1.53 | C(CH₃)(OH)CN | |
| 1.54 | CH(OCH₃)CN | |
| 1.55 | CH[OSi(CH₃)₃]CN | |
| 1.56 | CH(NH₂)CN | |
| 1.57 | CH(NH₂)COOCH₃ | |
| 1.58 | CH(NH₂)COOH | |
| 1.59 | COCOOH | |
| 1.60 | COCOOCH₃ | |
| 1.61 | COCOOC₂H₅ | |
| 1.62 | COCOOC₅H₁₁-n | |
| 1.63 | COC(OCH₃)₂COOCH₃ | |
| 1.64 | COC(OC₂H₅)COOC₂H₅ | m.p. 123–125° C. |
| 1.65 | C≡CH | |
| 1.66 | CH=NOCH₃ | m.p. 121–123° C. |
| 1.67 | CH=NOC₂H₅ | |
| 1.68 | CH=NOC₄H₉-i | |
| 1.69 | C(CH₃)=NOH | |
| 1.70 | C(CH₃)=NOCH₃ | |
| 1.71 | CH=NH | |
| 1.72 | CH=NCH₃ | |
| 1.73 | CH=N-phenyl | |
| 1.74 | CH=N-cyclohexyl | |
| 1.75 | CH=N-cyclopropyl | |

TABLE 1-continued

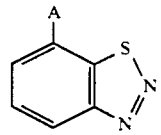

| Comp. No. | A | Physical data |
|---|---|---|
| 1.76 | CH=N-allyl | |
| 1.77 | C(CH₃)=N(3,5-diCl-phenyl) | |
| 1.78 | CH=N(3-NO₂-phenyl) | |
| 1.79 | CH=N(3-CF₃-phenyl) | m.p. 120–122° C. |
| 1.80 | CH₂—O—N=C(CH₃)₂ | |
| 1.81 | CH₂—O—N=C(CH₃)C₂H₅ | |
| 1.82 | CH₂ON=C(CN)CH₃ | |
| 1.83 | CH₂ON=C(CN)CONH₂ | m.p. 157–159° C. |
| 1.84 | CH₂ON=C(CN)CONHCONHC₂H₅ | |
| 1.85 | CH=N—NH₂ | m.p. 156–158° C. |
| 1.86 | CH=N—NH—C₂H₅ | |
| 1.87 | CH=N—N(CH₃)₂ | |
| 1.88 | CH=N—NH-phenyl | m.p. 167–168° C. |
| 1.89 | CH=N—NH-2,4,6-TriCl-phenyl | m.p. >250° C. |
| 1.90 | CH=N—NH-2,4,6-Di-Cl-phenyl | |
| 1.91 | CH=N—NH-cyclohexyl | |
| 1.92 | CH=N-benzyl | |
| 1.93 | C(CH₃)=N—NH-3-NO₂-phenyl | |
| 1.94 | COCN | |
| 1.95 | CH(OCH₃)COOCH₃ | |
| 1.96 | CH(Cl)COOCH₃ | |
| 1.97 | CH(Cl)COOC₂H₅ | |
| 1.98 | CH=CHCOOH | m.p. 199–202° C. |
| 1.99 | CH=C(CN)COOH | |
| 1.100 | CH=CHCN | |
| 1.101 | CH=C(CN)COOCH₃ | m.p. 150–153° C. |
| 1.102 | CH=C(COOC₂H₅)₂ | |
| 1.103 | CH₂—CH₂COOH | |
| 1.104 | CH₂—CH₂—COOCH₃ | |
| 1.105 | CH(Br)CH(Br)COOCH₃ | |
| 1.106 | C(NH₂)=NOH | m.p. 209–211° C. |
| 1.107 | COCCl₃ | $n_D^{26}$ = 1.6178 |
| 1.108 | CH(OH)CCl₃ | m.p. 163–164° C. |
| 1.109 | CH=CH—COOCH₃ | |
| 1.110 | CH₂NH₂ | m.p. 136–139° C. |
| 1.111 | CH=CH—CONH₂ | |
| 1.112 | C(OH)=NOCH₃ | m.p. 188–190° C. |
| 1.113 | CH₂SCOCH₃ | $n_D^{27}$ 1.6478 |
| 1.114 | CH₂SCO—C₆H₅ | |
| 1.115 | CH₂NHCH₃ | |
| 1.116 | CH₂N(CH₃)₂ | |
| 1.117 | CH₂NH—C₆H₅ | |
| 1.118 | CH₂N(CH₃)C₆H₄—(4-CH₃) | |
| 1.119 | CH₂NH(3,5-di-Cl—C₆H₃) | |
| 1.120 | CH(CH₃)NHC₆H₅ | |
| 1.121 | CH₂NH—NH—C₆H₅ | |
| 1.122 | CH₂NH—NH₂ | |
| 1.123 | CH₂NH—N(CH₃)₂ | |
| 1.124 | CH(Br)COOC₆H₅ | |
| 1.125 | COCH₂Br | m.p. 155–157° C. |
| 1.126 | C(NH₂)=NH.HCl | |
| 1.127 | C(CN)=NOH | m.p. 249–253° C. |
| 1.128 | C(CN)=NOCH₃ | |
| 1.129 | C(OH)—CF₃ | |
| 1.130 | CO—CF₃ | |
| 1.131 | C(=NH)—N(CH₃)₂(hydrogenoxalate) | |
| 1.132 | C(=NH)NH(3,5-di-Cl—C₆H₃).HCl | |
| 1.133 | CH(Cl)COOH | |
| 1.134 | CH(Cl)COOCH₃ | |
| 1.135 | CH(Br)COOC₂H₅ | |
| 1.136 | C(Cl)=C(Cl)COOCH₃ | |
| 1.137 | C(Cl)=C(Cl)₂ | |
| 1.138 | C(NH₂)(CH₃)CN | |
| 1.139 | C(CH₃)(NH₂)—COOCH₃ | |
| 1.140 | C(COOCH₃)(=CH—OH) | |
| 1.141 | C(COOCH₃)(=CH—OCH₃) | |
| 1.142 | C(CN)(=CH—OCH₃) | |
| 1.143 | C(=NH)(NH—NH₂) | |
| 1.144 | C(CH₃)—ON=C(CH₃)₂ | |
| 1.145 | CH=CH₂ | |
| 1.146 | CH≡CH—CH₃ | |
| 1.147 | CH=CCl₂ | |

TABLE 1-continued

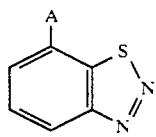

| Comp. No. | A | Physical data |
|---|---|---|
| 1.148 | C(Cl)=CCl₂ | |
| 1.149 | CHBr—CH₂Br | |

TABLE 2

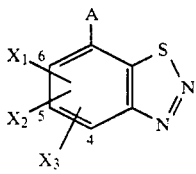

| Comp. No. | X₁, X₂, X₃ | A | Physical data |
|---|---|---|---|
| 2.1 | 6-Cl | CCl₃ | |
| 2.2 | 6-F | CF₃ | |
| 2.3 | 5-F | CF₃ | |
| 2.4 | 6-Br | CHO | |
| 2.5 | 6-F | CHO | |
| 2.6 | 6-F | CH₂O(CO)-phenyl | |
| 2.7 | 5-F | CH₂OCOCH₃ | |
| 2.8 | 4-F | COCH₃ | |
| 2.9 | 6-F | COCH₃ | |
| 2.10 | 4,5-di-F | CHO | |
| 2.11 | 5-F | CH₂OSO₂CH₃ | |
| 2.12 | 6-F | C(OCH₃)₃ | |
| 2.13 | 5,6-di-F | CH₂COOH | |
| 2.14 | 4-F | CH₂COS-phenyl | |
| 2.15 | 5-Br | CH(OH)COOH | |
| 2.16 | 6-Cl | CH[OSi(CH₃)₃]CN | |
| 2.17 | 4-Cl | CH=NOH | |
| 2.18 | 5-NO₂ | COCOOCH₃ | |
| 2.19 | 4-CH₃ | CH₂ON=C(CN)CONH₂ | |
| 2.20 | 5-F | CH=N-2'-Cl-benzyl | |
| 2.21 | 5-F | CH=CH—COOH | |
| 2.22 | 6-F | C(NH₂)=NOCH₃ | |
| 2.23 | 6-F | CH₂NH-cyclopropyl | |
| 2.24 | 6-F | CH₂NH—N(C₂H₅)₂ | |
| 2.25 | 6-Br | CH(Br)COO-benzyl | |
| 2.26 | 6-F | CH₂OCO-(2'-OH)—C₆H₄ | |
| 2.27 | 6-F | CH(OH)CH₃ | |
| 2.28 | 6-CH₃ | CHO | |
| 2.29 | 4,6-di-CH₃ | CHO | |
| 2.30 | 5-CH₃ | CH₂OCH₃ | |
| 2.31 | 5-CH₃ | CH₂OCOCH₃ | |
| 2.32 | 5-F | CHO | m.p. 129-131° C. |
| 2.33 | 6-SCH₃ | COCH₃ | |
| 2.34 | 5-SCH₃ | CHO | |
| 2.35 | 5-F | CH(OH)CCl₃ | m.p. 148-150° C. |
| 2.36 | 5-F | CH₂O(CO)-cyclopropyl | m.p. 74-76° C. |
| 2.37 | 4,6-di-F | CHO | |
| 2.38 | 6-F | CH₂CN | |
| 2.39 | 6-F | CH(NH₂)CN | |
| 2.40 | 6-F | C(N(CH₃)₂)=NH | |
| 2.41 | 5-F | C(COOCH₃)=CH—OH | |
| 2.42 | 5-F | C(COOCH₃)=CH—OMe | |
| 2.43 | 5-F | C(=NOH)NH₂ | |
| 2.44 | 4-F | CHO | |
| 2.45 | 5-F | C(=NOH)CN | |
| 2.46 | 5-F | C≡CH | |
| 2.47 | 5-F | CH(Cl)CCl₃ | |
| 2.48 | 6-F | CH=CH₂ | |
| 2.49 | 4-F | CH=CCl₂ | |

TABLE 3

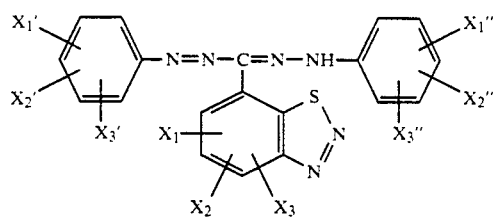

| Comp. No. | X₁, X₂, X₃ | X₁', X₂', X₃' | X₁'', X₂'', X₃'' | Physical data m.p. |
|---|---|---|---|---|
| 3.1 | — | — | — | 185-187° C. |
| 3.2 | — | 4-Cl | 4-Cl | |
| 3.3 | — | 4-NO₂ | — | |
| 3.4 | — | 3,5-di-Cl | — | |
| 3.5 | — | — | 2,4,6-triCl | |
| 3.6 | — | 3-CF₃ | — | |
| 3.7 | — | 3,5-di-CF₃ | 2F | |
| 3.8 | — | — | 3CF₃ | |
| 3.9 | — | — | 2,4-di-NO₂ | |
| 3.10 | — | 2-Me | 2 Br | |
| 3.11 | — | — | 2,6-di-Br | |
| 3.12 | — | 2-Cl | 4-Me | |
| 3.13 | 4-F | — | — | |
| 3.14 | 5-F | — | — | |
| 3.15 | 6-F | — | — | |
| 3.16 | 6-F | — | 2,4,6-tri-Cl | |
| 3.17 | 4,6-di-F | — | — | |
| 3.18 | 5,6-di-F | — | — | |
| 3.19 | 4,5-diF | — | — | |
| 3.20 | 4,5,6-triF | — | — | |
| 3.21 | 5-Br | 4-NO₂ | 2-Cl | |
| 3.22 | 5-NO₂ | — | — | |
| 3.23 | 6-OMe | 3-CF₃ | 3,5-di-Br | |
| 3.24 | 6-SMe | — | 6-NO₂ | |

TABLE 4

Compounds known from the literature whose use as fungicides is novel

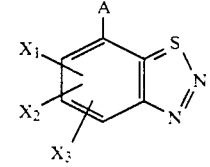

| Comp. No. | X₁, X₂, X₃ | A | Physical data |
|---|---|---|---|
| 4.1 | — | CHO | m.p. 134-138° C. |
| 4.2 | — | COCH₃ | m.p. 126-127° C. |
| 4.3 | 6-Cl | CHO | m.p. 148-150° C. |
| 4.4 | 6-SMe | CHO | m.p. 157-158° C. |
| 4.5 | 4-Br-6Cl | CHO | m.p. 131-133° C. |
| 4.6 | 6-OMe | CHO | m.p. 174-176° C. |
| 4.7 | — | CH=NOH | m.p. 230° C. |
| 4.8 | 6-OMe | CH=NOH | m.p. 217-218° C. |
| 4.9 | — | COCHBr₂ | m.p. 119-120° C. |

Formulation examples of active ingredients from the TABLES (% = percent by weight)

| 2.1 Wettable powder | a) | b) | c) |
|---|---|---|---|
| Active ingredient from the TABLES | 25% | 50% | 75% |
| Sodium lignin sulfonate | 5% | 5% | — |
| Sodium lauryl sulfate | 3% | — | 5% |
| Sodium diisobutylnaphthalene sulfonate | — | 6% | 10% |
| Octylphenol polyethylene glycol ether (7-8 mol of ethylene oxide) | — | 2% | — |
| Highly-disperse silica | 5% | 10% | 10% |

-continued

| Formulation examples of active ingredients from the TABLES (% = percent by weight) | | | |
|---|---|---|---|
| 2.1 Wettable powder | a) | b) | c) |
| Kaolin | | 62% | 27% |

The active ingredient is mixed with the additives and ground in a suitable mill until homogeneous. This gives wettable powders which can be diluted with water to give suspensions of any desired concentration.

| 2.2 Emulsion concentrate | |
|---|---|
| Acitve ingredient from the TABLES | 10% |
| Octylphenol polyethylene glycol ether (4-5 mol of ethylene oxide) | 3% |
| Calcium dodecylbenzene sulfonate | 3% |
| Castor oil polyglycol ether (35 mol of ethylene oxide) | 4% |
| Cyclohexanone | 30% |
| Xylene mixture | 50% |

Emulsions of any desired concentration can be prepared from this concentrate by dilution with water.

| 2.3 Dusts | a) | b) |
|---|---|---|
| Active ingredient from the TABLES | 5% | 8% |
| Talc | 95% | — |
| Kaolin | — | 92 |

Ready-for-use dusts are obtained by mixing the active ingredient with the carriers and grinding the mixture on a suitable mill.

| 2.4 Extruder granules | |
|---|---|
| Active ingredient from the TABLES | 10% |
| Sodium lignin sulfonate | 2% |
| Carboxymethyl cellulose | 1% |
| Kaolin | 87% |

The active ingredient is mixed with the additives, and the mixture is ground and moistened with water. This mixture is extruded and subsequently dried in a stream of air.

| 2.5 Coated granules | |
|---|---|
| Active ingredient from the TABLES | 3% |
| Polyethylene glycol (MW 200) | 3% |
| Kaolin | 94% |

(MW = molecular weight)

The kaolin is moistened with polyethylene glycol and, in a mixer, coated uniformly with the finely ground active ingredient. In this manner, dust-free coated granules are obtained.

| 2.6 Suspension concentrate | |
|---|---|
| Active ingredient from the TABLES | 40% |
| Ethylene glycol | 10% |
| Nonylphenol polyethylene glycol ether (15 mol ethylene oxide) | 6% |
| Sodium lignin sulfonate | 10% |
| Carboxymethyl cellulose | 1% |
| 37% aqueous formaldehyde solution | 0.2% |
| Silicone oil in the form of a 75% aqueous emulsion | 0.8% |

-continued

| 2.6 Suspension concentrate | |
|---|---|
| Water | 32% |

The finely ground active ingredient is mixed intimately with the additives. This gives a suspension concentrate from which suspensions of any desired concentration can be prepared by dilution with water.

3. BIOLOGICAL EXAMPLES

EXAMPLE 3.1

Activity against *Colletotrichum lagenarium* on *Cucumis sativus* L.

a) Cucumber plants are grown for 2 weeks and then sprayed with a spray mixture prepared with a wettable powder of the active ingredient (concentration: 200 ppm). After 48 hours, the plants are infected with a spore suspension ($1.5 \times 10^5$ spores/ml) of the fungus and incubated for 36 hours at high atmospheric humidity and a temperature of 23° C. The incubation is then continued at normal atmospheric humidity and 22° C. to 23° C.

The protective action is assessed 7-8 days after the infection, using the fungus infestation as parameter.

b) Cucumber plants are grown for 2 weeks and then treated with a spray mixture prepared with a wettable powder of the active ingredient by soil application (concentration: 60 or 20 ppm, relative to the soil volume). After 48 hours, the plants are infected with a spore suspension ($1.5 \times 10^5$ spores/ml) of the fungus and incubated for 36 hours at high atmospheric humidity and a temperature of 23° C. The incubation is then continued at normal atmospheric humidity and 22° C.

The protective action is assessed 7-8 days after the infection, using the fungus infestation as parameter.

c) Cucumber plants are grown for 2 weeks and then sprayed with a spray mixture prepared with a wettable powder of the active ingredient (concentration: 200 ppm).

After 3 weeks, the plants are infected with a spore suspension ($1.5 \times 10^5$ spores/ml) of the fungus and incubated for 36 hours at high atmospheric humidity and a temperature of 23° C. The incubation is then continued at normal atmospheric humidity and 22° C. to 23° C.

The protective action is assessed 7-8 days after the infection, using the fungus infestation as parameter.

In tests (a) and (b), good activity is shown by compounds from Tables 1 to 4. For example, compounds 1.2, 1.6, 1.7, 1.12, 1.33, 1.38, 1.64, 1.79, 1.83, 1.85, 1.89, 1.91, 1.106, 1.108, 1.110, 1.113, 1.125, 1.127.3.1, 4.1 and 4.2 reduce fungus infestation to 0 to 20%. In contrast, untreated, but infected control plants show Colletotrichum infestation of 100%.

EXAMPLE 3.2

Activity against *Phytophthora infestans* on tomato plants a) Tomato plants are grown for 3 weeks and then sprayed with a spray mixture prepared with a wettable powder of the active ingredient (0.02% active substance). After 24 hours, the treated plants are infected with a sporangia suspension of the fungus. Fungus infestation is assessed after incubation of the infected plants for 5 days at 90-100% relative atmospheric humidity and 20° C.

b) Tomato plants are grown for 3 weeks, and a spray mixture prepared with a wettable powder of the active ingredient is then poured near them (0.006% active substance relative to the soil volume). Care is taken that the spray mixture does not come into contact with the above ground parts of the plants. After 48 hours, the treated plants are infected with a sporangia suspension of the fungus. The fungus infestation is assessed after incubation of the infected plants for 5 days at 90–100% relative atmospheric humidity and 20° C.

Compounds from Tables 1 to 4 show good protective action against the Phytophthora fungus. For example, fungus infestation is reduced to 0 to 20% in test a) by compounds 1.6, 1.31, 1.38, 1.83, 1.127 and 4.1 and in test b) by 1.1, 1.6, 1.12, 1.31, 1.38, 1.83, 1.85, 1.101 and 1.106. In contrast, untreated, but infected control plants show Phytophthora infestation of 100%.

EXAMPLE 3.3

Activity against *Pyricularia oryzae* on rice plants a) Rice plants are grown for 2 weeks and then sprayed with a spray mixture prepared with a wettable powder of the active ingredient (0.02% active substance). After 48 hours, the treated plants are infected with a conidia suspension of the fungus. Fungus infestation is assessed after incubation for 5 days at 95–100% relative atmospheric humidity and 24° C.

b) A spray mixture prepared with a wettable powder of the active ingredient (0.006% active substance relative to the soil volume) is poured near rice plants aged 2 weeks. The pots are then filled with water to such an extent that the lower portions of the stems of the rice plants are immersed in the water. After 96 hours, the treated rice plants are infected with a conidia suspension of the fungus. Fungus infestation is assessed after incubation of the infected plants for 5 days at 95–100% relative atmospheric humidity and approx. 24° C.

Compared with untreated control plants (100% infestation) rice plants which have been treated with a spray mixture comprising, as active substance, a compound from Tables 1 to 4, only show a low level of fungus infestation. For example, the infestation is reduced to 0 to 20% in test (a) by compounds 1.6, 1.98, 1.101 and 4.1 and in test (b) by compounds 1.6, 1.64, 1.66, 1.101, 4.1 and 4.7.

EXAMPLE 3.4

Activity against *Peronospora tabacina* on tobacco plants

A) Foliar application

Tobacco plants (8 weeks old) are sprayed with a formulated solution of the active ingredient (concentration: 0.02% active substance). Four days after the treatment, the plants are inoculated with a sporangia suspension of *Peronospora tabacina* ($10^4$ sporangia/ml), kept for 20 hours in the dark at 25° C. and high atmospheric humidity, and then incubated further with normal day/night rythm.

B) Soil application

Tobacco plants (8 weeks old) are treated with a formulated solution of the active ingredient by soil application (concentration: 0.006% active substance relative to the soil volume). After 4 days, the plants are inoculated with a sporangia suspension of *Peronospora tabacina* ($10^4$ sporangia/ml), kept for 20 hours in the dark at 25° C. and high atmospheric humidity, and then incubated further with normal day/night rythm.

The symptoms in tests A and B are assessed using the fungus-infested leaf area as parameter.

The control plants show infestation of 90 to 100%. Plants which have been treated with compound 1.6 or 4.1 in test A, show infestation of 0–30%.

EXAMPLE 3.5

Activity against *Bremia lactucae* in lettuce

A formulated solution of the active ingredient (0.002% active substance relative to the soil volume) is poured near lettuce plants aged two weeks. After 5 days, the treated plants are inoculated with a spore suspension of the fungus ($5 \times 10^4$ s/ml). The plants are incubated at 18° C., first under a cover (relative atmospheric humidity 90–100%) for 2 days, then without cover for 7 days. To induce sporulation of the fungus, the plants are again placed under a cover for 3 days.

Fungus infestation is assessed 12 days after inoculation, using the fungus-infested leaf area as parameter.

Compounds from Tables 1 to 4 show good activity against Bremia. For example, plants which have been treated with compounds 1.1, 1.2, 1.6, 1.98 or 4.1, remain largely free from infestation (damage 0–30%). In contrast, untreated, but infected plants (control) show a Bremia infestation of 100%.

EXAMPLE 3.6

Activity against *Erysiphe graminis* in wheat

Protective Action:

Wheat plants, 17 days old, are sprayed with a formulated solution of the active ingredient (0.02% active substance). Immediately after the treatment, the plants are incubated under cylindrical covers. After 24 hours, the plants are uncovered. After a further 3 days, the treated plants are cut above the primary leaf. The primary leaves are positioned horizontally and, in an inoculation tower, inoculated with spores of *Erysiphe graminis* (spore density: 0.2 mg per m$^2$). The test is carried out in a controlled-environment cabinet with 12 h light (18 KLux), 20° C. and 12 h darkness, 18° C.

The infestation is assessed 9 and 13 days after inoculation.

In this test, compounds from Tables 1 to 4 used as active ingredient show a good activity against *Erysiphe graminis*. For example, plants which have been treated with compound 1.1, 1.2, 1.6, 1.7, 1.12, 1.31, 1.33, 1.38, 1.66, 1.83, 1.98, 1.108, 4.1 or 4.2 remain largely free from Erysiphe infestation (damage 0 to 20%). In contrast, untreated, but infected plants (control) show Erysiphe infestation of 100%.

EXAMPLE 3.7

Activity against *Cercospora arachidicola* on peanut plants

Peanut plants, 10–15 cm in height, are sprayed with a spray mixture prepared with a wettable powder of the active ingredient (0.02% active substance) and, after 48 hours, infected with a conidia suspension of the fungus. The infected plants are incubated for 72 hours at approx. 21° C. and high atmospheric humidity, and subsequently placed in a greenhouse until the typical lesions on the leaves appear. The fungicidal activity is assessed 12 days after infection, using number and size of the lesions as parameter.

Compared with untreated, but infected control plants (number and size of lesions=100%), peanut plants which have been treated with active ingredients from Tables 1 to 4 show substantially reduced Cercospora infestation. For example, in the above experiments, compounds Nos. 1.83, 1.85, 1.108, 1.125, 1.127, 3.1 and 4.7 largely prevent the occurrence of lesions (0-20%).

EXAMPLE 3.8

Activity against *Puccinia graminis* in wheat a) Residual-Protective Action 6 days after sowing, wheat plants are sprayed with a spray mixture prepared with a wettable powder of the active ingredient (0.02% active substance). 24 hours later, the treated plants are infected with a ureido spore suspension of the fungus. After incubation for 48 hours at 95-100% relative atmospheric humidity and approx. 20° C., the infected plants are placed in a greenhouse at approx. 22° C. The development of rust pustules is assessed 12 days after infection.

b) Systemic Action 5 days after sowing, a spray mixture prepared with a wettable powder of the active ingredient (0.006% active substance relative to the soil volume) is poured near wheat plants. After 48 hours, the treated plants are infected with a ureido spore suspension of the fungus. After incubation for 48 hours at 95-100% relative atmospheric humidity and approx. 20° C., the infected plants are placed in a greenhouse at approx. 22° C. The development of rust pustules is assessed 12 days after infection.

Untreated, but infected control plants show Puccinia infestation of 100%. Compounds from Tables 1 to 4 show good action against Puccinia fungi.

For example, fungus infestation was reduced to less than 20% in test a) by compounds Nos. 1.7, 1.8, 1.31, 1.64, 1.79, 1.83, 1.98, 1.113, 1.125, 1.127 and in test b) by No. 1.113.

EXAMPLE 3.9

Action against *Pseudomonas lachrymans* on *Cucumis sativus* L.

A) Foliar Application

Cucumber plants are grown for 2 weeks and then sprayed with a spray mixture prepared with a wettable powder of the active ingredient (concentration: 0.02% active substance).

After 1 week, the plants are infected with a bacteria suspension ($10^8$ bacteria/ml) and incubated for 7 days at high atmospheric humidity and a temperature of 23° C.

The protective action is assessed 7-8 days after infection, using bacterial infestation as parameter.

Compounds from Tables 1 to 4 provide good protection against *Pseudomonas lachrymans*. For example, plants which have been treated with compound 1.31, 1.38, 1.108 or 4.2 remain largely free from Pseudomonas (infestation 20 to 0%).

B) Soil Application

Cucumber plants are grown for 2 weeks and then treated by soil application with a spray mixture prepared with a wettable powder of the active ingredient (concentration: 0.002% active substance relative to the soil volume).

After 1 week, the plants are infected with a bacteria suspension ($10^8$ bacteria/ml) and incubated for 7 days at high atmospheric humidity and a temperature of 23° C.

The protective action is assessed 7-8 days after infection, using bacterial infestation as the parameter.

Compounds from Tables 1 to 4 effect good immunisation against *Pseudomonas lachrymans*. For example, plants which have been treated for example with compound 1.31, 1.33, 1.38 or 1.108 remain virtually completely free from Pseudomonas (infestation 20 to 0%).

In tests A and B, untreated, but infected control plants show a disease level of 100%.

EXAMPLE 3.10

Activity against *Plasmopara viticola* on grape vine

Grape vine seedlings in the 4-5 leaf stage are sprayed with a spray mixture prepared with a wettable powder of the active ingredient (0.02% active substance). After 1 week, the treated plants are infected with a sporangia suspension ($5 \times 10^4$ sporangia/ml) of the fungus. The protective action is assessed after incubation for 6 days at 95-100% relative atmospheric humidity and 20° C.

In this test, untreated, but infected control plants show an infestation of 100%.

Compounds from Tables 1 to 4 effect good immunisation against *Plasmopara viticola*. For example, grape vines which have been treated for example with compound 1.83 or 1.125 remain largely free from *Plasmopara viticola* (infestation 20 to 0%).

EXAMPLE 3.11

Activity against *Cercospora nicotianae* on tobacco plants

Foliar Application

Tobacco plants (8 weeks old) are sprayed with a formulated solution of the active ingredient (concentration: 200 ppm). Four days after the treatment, the plants are inoculated with a spore suspension of *Cercospora nicotianae* ($10^5$ spores/ml) and incubated for 5 days at high atmospheric humidity and a temperature of 22°-25° C. The incubation is then continued at normal atmospheric humidity and 20°-22° C.

The symptoms in the test are assessed 12-14 days after infection, using fungus infestation as parameter.

The control plants show infestation of 100%. Plants which have been treated with compounds 1.83, 1.85, 1.108, 1.125, 1.127, 3.1 or 4.7 show infestation of 0-20%.

EXAMPLE 3.12

Activity against *Pythium ultimum* on Zea maize (maize, cv. Sweet Corn)

Test principle: Soil fungus: protective-local soil application.

Test method: Mycelium of *Pythium ultimum* mixed with soil (500 ml mycelium suspension per 10 liters of soil), and 250 ml plastic dishes are filled with the fungus/soil mixture. After incubation for 4 days at 10° C., 10 kernels of the test plant (maize) are placed into each dish. On the following day, the dishes which have been prepared in this way are each irrigated with 50 ml of spray solutions prepared with 25% wettable powder and water comprising 20; 6; 2; 0.6; 0.2; 0.006 and 0.02 ppm of active substance. After an incubation phase of 7 days at 10° C. and a subsequent incubation phase of 4 days at 22° C., the effect of the test substances is assessed by numeric determination of the emergence of the test plants.

Compounds from Tables 1-4 show good activity against *Pythium ultimum*. For example, compound 1.125 shows an activity of above 80%.

What is claimed is:

1. A compound of the formula

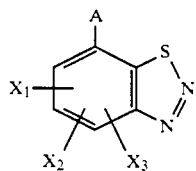

(I)

in which:
- $X_1$, $X_2$ and $X_3$ independently of one another are hydrogen, methyl, methoxy, methylthio, halogen or nitro;
- A is $C_1$-$C_2$alkyl which is substituted by a minimum of 1 and a maximum of 3 X—$C_1$-$C_4$alkyl groups, methyl which is substituted by 2 or 3 halogen atoms, ethyl which is substituted by hydroxyl and/or not more than 4 halogen atoms, vinyl which is unsubstituted or substituted by not more than 3 halogen atoms; furthermore ethynyl, propargyl, formyl, acetyl, acetyl which is substituted by not more than 3 halogen atoms, or one of the groups C(R)=N—N($R_2$)$R_3$, C(N=N—$U_1$)=N—N-H—$U_1$, CH(R)—[N($R_1$)]$_n$—N($R_2$)$R_3$, C(R)(CN)O$R_4$, C(R)=N(O)$_n$$R_3$, CH(R)—O—N=C($R_1$)$R_2$, CH(R)—O—N=C(CN)—CONH—$R_5$, C($R_6$)=N—(O)$_n$R, CH(R)—Y—E—$R_3$, CO—[C(OR)$_2$]$_n$Q, C(Q)=CH—OR or T—Q; in which furthermore:
- n is zero or 1;
- X and Y independently of one another are oxygen or sulfur;
- R and $R_1$ independently of one another are hydrogen or $C_1$-$C_2$alkyl;
- $R_2$ is hydrogen, $C_1$-$C_8$alkyl, $C_3$-$C_6$alkenyl, $C_3$-$C_6$alkynyl, $C_3$-$C_7$cycloalkyl, benzyl or cyano;
- $R_3$ is hydrogen, $C_1$-$C_6$alkyl, $C_3$-$C_6$alkenyl, $C_3$-$C_6$alkynyl, $C_3$-$C_7$cycloalkyl, benzyl or is an aryl radical U;
- $R_4$ is hydrogen, $C_1$-$C_6$alkyl, Si($C_1$-$C_6$alkyl)$_3$ or OCO$C_1$-$C_3$alkyl;
- $R_5$ is hydrogen or CONH$R_1$;
- $R_6$ is N($R_1$)$R_2$, hydrazino or Q;
- E is CO or SO$_2$;
- U and $U_1$ independently of one another are a phenyl radical which is unsubstituted or monosubstituted or polysubstituted by identical or different substituents from the series comprising methyl, methoxy, halogen, trifluoromethyl, nitro or cyano;
- T is $C_1$-$C_2$alkylene, methylene which is substituted by amino, hydroxyl or halogen, the substituents being independent of one another, or is ethenylene which is unsubstituted or substituted by halogen or cyano;
- Q is COXR or cyano, with the exception of the following compounds:
  7-formyl-1,2,3-benzothiadiazole;
  7-acetyl-1,2,3-benzothiadiazole;
  6-chloro-7-formyl-1,2,3-benzothiadiazole;
  6-methylthio-7-formyl-1,2,3-benzothiadiazole;
  4-bromo-6-chloro-7-formyl-1,2,3-benzothiadiazole;
  6-methoxy-7-formyl-1,2,3-benzothiadiazole;
  7-hydroxyiminomethyl-1,2,3-benzothiadiazole;
  6-methoxy-7-hydroxyiminomethyl-1,2,3-benzothiadiazole,
  7-dibromoacetyl-1,2,3-benzothiadiazole.

2. A compound of the formula I

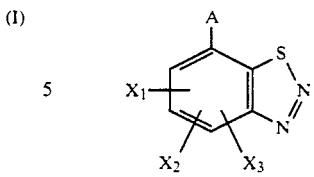

(I)

in which:
- $X_1$, $X_2$ and $X_3$ independently of one another are hydrogen or fluorine;
- A is $C_1$-$C_2$alkyl which is substituted by a minimum of 1 and a maximum of 3 X—$C_1$-$C_4$alkyl groups, methyl which is substituted by 2 or 3 halogen atoms, ethyl which is substituted by hydroxyl and/or not more than 4 halogen atoms, or formyl, acetyl, or one of the groups C(R)=N—N($R_2$)$R_3$, CH(R)—[N($R_1$)]$_n$—N($R_2$)$R_3$, C(R)(CN)O$R_4$, C(R)=N(O)$_n$$R_3$, CH(R)—O—N=C($R_1$)$R_2$, CH(R)—O—N=C(CN)—CONH—$R_5$, C($R_6$)=N—(O)$_n$R, CH(R)—Y—E—$R_3$, CO—[C(OR)$_2$]$_n$COXR, C(Q)=CH—OR or T—Q; in which furthermore:
- n is zero or 1;
- X and Y are oxygen;
- R and $R_1$ independently of one another are hydrogen or $C_1$-$C_2$alkyl;
- $R_2$ is hydrogen, $C_1$-$C_4$alkyl, $C_3$-$C_4$alkenyl, $C_3$-$C_4$alkynyl, $C_3$-$C_6$cycloalkyl or benzyl;
- $R_3$ is hydrogen, $C_1$-$C_4$alkyl, $C_3$-$C_4$alkenyl, $C_3$-$C_4$alkynyl, $C_3$-$C_6$cycloalkyl or a phenyl radical which is substituted by identical or different substituents from the series comprising methyl, halogen or trifluoromethyl;
- $R_4$ is hydrogen, $C_1$-$C_3$alkyl or Si($C_1$-$C_2$alkyl)$_3$;
- $R_5$ is hydrogen or CONH$C_1$-$C_3$alkyl;
- $R_6$ is amino or cyano;
- E is CO;
- T is methylene, methylene which is substituted by amino or ethenylene;
- Q is COOR or cyano, with the exception of the following compounds:
  7-formyl-1,2,3-benzothiadiazole;
  7-acetyl-1,2,3-benzothiadiazole;
  6-chloro-7-formyl-1,2,3-benzothiadiazole;
  6-methylthio-7-formyl-1,2,3-benzothiadiazole;
  4-bromo-6-chloro-7-formyl-1,2,3-benzothiadiazole;
  6-methoxy-7-formyl-1,2,3-benzothiadiazole;
  7-hydroxyiminomethyl-1,2,3-benzothiadiazole;
  6-methoxy-7-hydroxyiminomethyl-1,2,3-benzothiadiazole,
  7-dibromoacetyl-1,2,3-benzothiadiazole.

3. A compound of the formula I

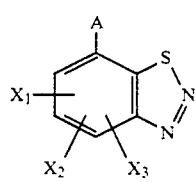

(I)

in which:
- $X_1$, $X_2$ and $X_3$ are hydrogen;
- A is methyl which is substituted by a minimum of 1 and a maximum of 2 X—$C_1$-$C_4$alkyl groups, methyl which is substituted by 2 or 3 fluorine or chlorine atoms, ethyl which is substituted by hydroxyl or chlorine, or formyl, acetyl, or one of the groups C(R)=N—N(R$_2$)R$_3$, CH(R)—[N(R$_1$)-]$_n$—N(R$_2$)R$_3$, C(R)(CN)OR$_4$, C(R)=N(O)$_n$R$_3$, CH(R)—O—N=C(R$_1$)R$_2$, CH(R)—O—N=C(CN)—CONHR$_5$, C(R$_6$)=N—OR, CH(R)—Y—E——R$_3$, CO[C(OR)$_2$]$_n$COXR, C(COOR)=CH—OR or T—Q; in which furthermore:

n is 1;
X is oxygen;
R and R$_1$ independently of one another are hydrogen or methyl;
R$_2$ is hydrogen, C$_1$-C$_2$alkyl, allyl, propargyl, cyclopropyl or benzyl;
R$_3$ is hydrogen, C$_1$-C$_2$alkyl, allyl, propargyl, cyclopropyl, or a phenyl radical which is substituted by identical or different substituents from the series comprising methyl, fluorine, chlorine or trifluoromethyl;
R$_4$ is hydrogen, C$_1$-C$_2$alkyl or Si(CH$_3$)$_3$;
R$_5$ is hydrogen or CONH-C$_1$-C$_2$alkyl;
R$_6$ is amino;
Y is oxygen;
E is CO;
T is methylene or cyano, with the exception of the following compounds:
7-formyl-1,2,3-benzothiadiazole;
7-acetyl-1,2,3-benzothiadiazole;
6-chloro-7-formyl-1,2,3-benzothiadiazole;
6-methylthio-7-formyl-1,2,3-benzothiadiazole;
4-bromo-6-chloro-7-formyl-1,2,3-benzothiadiazole;
6-methoxy-7-formyl-1,2,3-benzothiadiazole;
7-hydroxyiminomethyl-1,2,3-benzothiadiazole;
6-methoxy-7-hydroxyiminomethyl-1,2,3-benzothiadiazole,
7-dibromoacetyl-1,2,3-benzothiadiazole.

4. A compound of the formula I

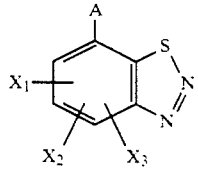

in which:
X$_1$, X$_2$ and X$_3$ are hydrogen;
A is methyl which is substituted by a minimum of 1 and a maximum of 2 X—C$_1$-C$_2$alkyl groups, methyl which is substituted by 2 or 3 fluorine atoms, ethyl which is substituted by hydroxyl or chlorine, or formyl, or one of the groups C(R)=N—N(R$_2$)R$_3$, CH(R)—[N(R$_1$)-]$_n$—N(R$_2$)R$_3$, C(R)(CN)OR$_4$, C(R)=N—R$_3$, CH(R)—O—N=C(R$_1$)R$_2$, C(R$_6$)=N—OR, CH(R)—Z—E—R$_3$, CO[C(OR)$_2$]$_n$COXR or T—Q; in which furthermore:
n is 1;
X is oxygen;
R and R$_1$ independently of one another are hydrogen or methyl;
R$_2$ is hydrogen, methyl, allyl, cyclopropyl or benzyl;
R$_3$ is hydrogen, methyl, allyl, cyclopropyl, or a phenyl radical which is substituted by identical or different substituents from the series comprising methyl, fluorine, chlorine or trifluoromethyl;
R$_4$ is hydrogen, methyl or Si(CH$_3$)$_3$;
R$_5$ is hydrogen or CONH—CH$_2$—CH$_3$;
R$_6$ is amino;
Y is oxygen;
E is CO;
T is methylene;
Q is COOCH$_3$ or cyano, with the exception of the following compounds:
7-formyl-1,2,3-benzothiadiazole;
7-acetyl-1,2,3-benzothiadiazole;
6-chloro-7-formyl-1,2,3-benzothiadiazole;
6-methylthio-7-formyl-1,2,3-benzothiadiazole;
4-bromo-6-chloro-7-formyl-1,2,3-benzothiadiazole;
6-methoxy-7-formyl-1,2,3-benzothiadiazole;
7-hydroxyiminomethyl-1,2,3-benzothiadiazole;
6-methoxy-7-hydroxyiminomethyl-1,2,3-benzothiadiazole,
7-dibromoacetyl-1,2,3-benzothiadiazole.

5. A compound of the formula

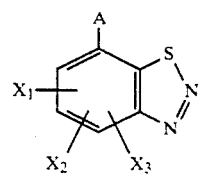

selected from the group:
7-acetoxymethyl-1,2,3-benzothiadiazole;
7-[2-cyanoacetamidyl0iminooxymethyl]-1,2,3-benzothiadiazole;
7-(N-methoxyiminomethyl)-1,2,3-benzothiadiazole;
7-(N-methoxyiminohydroxymethyl)-1,2,3-benzothiadiazole;
7-methoxymethyl-1,2,3-benzothiadiazole;
3-(7-benzo-1,2,3-thiadiazolyl)acrylic acid;
7-cyanomethyl-1,2,3-benzothiadiazole;
7-trichloromethyl-1,2,3-benzothiadiazole;
7-dichloromethyl-1,2,3-benzothiadiazole;
benzo-1,2,3-thiadiazole-7-(N-hydroxycarboximideamide);
benzo-1,2,3-thiadiazole-7-(N-methoxyhydroxamic acid);
2-(benzo-1,2,3-thiadiazolyl)-2-hydroxyiminoacetonitrile;
5-fluoro-benzo-1,2,3-thiadiazole-7-carbaldehyde;
6-fluoro-benzo-1,2,3-thiadiazole-7-carbaldehyde;
4-fluoro-benzo-1,2,3-thiadiazole-7-carbaldehyde;
N,N-diphenyl-C-[benzo-1,2,3-thiadiazol-7'yl]formazan;
7-(bromoacetyl)benzo-1,2,3-thiadiazole.

* * * * *